US007364735B1

(12) United States Patent
Voorberg et al.

(10) Patent No.: US 7,364,735 B1
(45) Date of Patent: Apr. 29, 2008

(54) METHOD FOR DIAGNOSIS AND TREATMENT OF HAEMOPHILIA A PATIENTS WITH AN INHIBITOR

(75) Inventors: Johannes Jacobus Voorberg, Assendelft (NL); Edward Norbert van den Brink, Amsterdam (NL); Ellen Anne Maria Turenhout, Noordwijkerhout (NL)

(73) Assignee: Stichting Sanquin Bloedvoorziening, Amsterdam (NL)

( * ) Notice: Subject to any disclaimer, the term of this patent is extended or adjusted under 35 U.S.C. 154(b) by 0 days.

(21) Appl. No.: 09/674,752

(22) PCT Filed: May 7, 1999

(86) PCT No.: PCT/NL99/00285

§ 371 (c)(1),
(2), (4) Date: Dec. 29, 2000

(87) PCT Pub. No.: WO99/58680

PCT Pub. Date: Nov. 18, 1999

(30) Foreign Application Priority Data

May 8, 1998 (EP) ................................. 98201543

(51) Int. Cl.
A61K 39/395 (2006.01)
G01N 33/53 (2006.01)
C07K 16/46 (2006.01)

(52) U.S. Cl. ............................... 424/145.1; 530/387.3; 530/388.25; 435/7.1

(58) Field of Classification Search ............. 530/387.3, 530/388.25, 389.3; 424/133.1, 135.1, 142.1, 424/145.1; 435/7.1
See application file for complete search history.

(56) References Cited

U.S. PATENT DOCUMENTS

| 4,731,245 A | * | 3/1988 | Tsurumizu et al. |
| 5,543,145 A | | 8/1996 | Saint-Remy et al. |
| 5,916,771 A | * | 6/1999 | Hori et al. |
| 6,632,927 B2 | * | 10/2003 | Adair et al. |

FOREIGN PATENT DOCUMENTS

| EP | 0 152 746 | | 8/1985 |
| EP | 0 659 766 A1 | | 6/1995 |
| WO | WO 93/03151 | | 2/1993 |
| WO | WO 93/12232 | | 6/1993 |
| WO | WO 95/08336 | * | 3/1995 |
| WO | WO 96/05860 | | 2/1996 |
| WO | WO 96/16974 | | 6/1996 |

OTHER PUBLICATIONS

Panka et al. Variable region framework differences result in decreased or increased affinity of variant anti-digoxin antibodies. Proc Natl Acad Sci U S A. 85(9):3080-3084, 1988.*
Rudikoff S et al., Single amino acid substitution altering antigen-binding specificity. Proc Natl Acad Sci U S A. 79(6):1979-1983 1982.*
Amit et al., Three-dimensional structure of an antigen-antibody complex at 2.8 A resolution. Science. 233(4765):747-753, 1986.*
Lenting et al., Identification of a binding site for blood coagulation factor IXa on the light chain of human factor VIII. J Biol Chem. 269(10):7150-7155, 1994.*
Bird et al. Single-chain antigen-binding proteins. Science. 242(4877):423-426, 1988.*
Scandella D., Human antibodies which Inactivate Factor VIII: Their Epitope Specificity and Biochemical and Functional Characteristics. International Journal of Pediatric Hematology/Oncology, 1:437-447, 1994.*
Davies et al Primary struture of the variable domains of factor VIII antibodies obtained from inhibitor patient B cell RNA by V gene phage display technology. thromb. Haemostas. Supplement: 2352, 1997.*
Foung et al (1986). Generation of Human monoclonal . . . , Chapter 13. In Methods in Enzymology vol. 121, Immunochemical Techniques, Part I, Hubridoma Technology and Monoclonal Antibodies, Langone and Vunakis Editors, Academic Press, Inc. New York pp. 168-174.*
Leon W. Hoyer, M.D., "Future Approaches to Factor VIII Inhibitor Therapy," *The American Journal of Medicine* (1991) 91: 40S-44S.
Karin Fijnvandraat, Patrick H.N. Celie, Ellen A.M. Turenhout, Jan W. ten Cate, Jan A. van Mourik, Koen Mertens, Marjolein Peters, and Jan Voorberg, "A Human Alloantibody Interferes With Binding of Factor Ixa to the Factor VIII Light Chain," *Blood* (1998) 91: 2347-2352.
Jean Guy G. Gilles, Jef Arnout, Jos Vermylen, and Jean-Marie R. Saint-Remy, "Anti-Factor VIII Antibodies of Hemophiliac Patients Are Frequently Directed Towards Nonfunctional Determinants and Do Not Exhibit Isotypic Restriction," *Blood* (1993) 82: 2452-2461.
Yvette Sultan, "Acquired hemophilia and its treatment," *Blood Coagulation and Fibrinolysis* (1997) 8:S15-S18.

(Continued)

*Primary Examiner*—Maher M. Haddad
(74) *Attorney, Agent, or Firm*—Hoffman & Baron, LLP

(57) ABSTRACT

A polynucleotide, comprising a contiguous nucleotide sequence coding for a human antibody with factor VIII specificity, or complementary to a nucleotide sequence coding for a human antibody for factor VIII specificity, or capable of selectively hybridizing under stringent conditions to such nucleotide sequence. Such polynucleotide may be used as a probe or primer for detection of factor VIII inhibitors, or be used for producing a recombinant polypeptide. A polypeptide, comprising a contiguous amino acid sequence corresponding to or mimicking a fragment or derivative of a human antibody with factor VIII specificity capable of specific binding to factor VIII. An antibody, comprising a recombinant human antibody with factor VIII specificity or an anti-idiotypic antibody directed against a human antibody with factor VIII specificity. Pharmaceutical compositions which contain such polypeptide or antibody.

13 Claims, 20 Drawing Sheets

OTHER PUBLICATIONS

James D. Marks, Hennie R. Hoogenboom, Timothy P. Bonnert, John McCafferty, Andrew D. Griffiths and Greg Winter, "By-passing Immunization Human Antibodies from V-gene Libraries Displayed on Phage," *J. Mol. Biol.* (1991) 222: 581-597.

Angray S. Kang, et al., "Antibody Redesign by Chain Shuffling from Random Combinatorial Immunoglobulin Libraries", *Proc. Natl. Acad. Sci.* 1997, 88:11120-11123.

Heather M. Griffin, et al., "A Human Monoclonal Antibody Specific for the Leucine-33 Form of Platelet Glycoprotein IIIa From a V Gene Phage Display Library", *Blood,* 1995, 86(12): 4430-4436.

* cited by examiner

Figure 3

```
                      FR1                            CDR1           FR2                CDR2                        FR3                                   CDR3                   FR4
            ------------------------------     ----------    ----------------    --------------------    -----------------------------------    -------------------------    ----------
                     1         2         3          1             4         5            6                    7         8         9                         1                        1
            123456789012345678901234567890     1ab2345    6789012345689    012abc34567890123 45     67890123456789012abc34567890 1234      567890abcdefghijklm12     34567890123

VH EL-14    QVQLVQSGAEAKKPGSSVKVSCKASGDTFN     S--FPIS    WVRQAPGQGLEWMG    GIIP--IFGSTKYAQKFQG     RVTMTADGSTSTAYMELNSLRSEDTAIYYCAR        QQNGGWYEGPLLEPRPDALDI       WGQGTMVTVSS
DP-10       ------V-----------------G--S       ---YA--    --------------    ---TAN---------I--      ----I---E---------------S--V----        ---------------------       -----------

1                             1
                     1         2         3          1             4         5            6                    7         8         9                    0                            0
            123456789012345678901234567890     1ab2345    6789012345689    012abc34567890123 45     67890123456789012abc34567890 1234      567890abcdefghijklmno12     34567890123

VH IT-2     QVQLLQSATEVKKPGASMKVSCMASGYPFT     S--YDIS    WVRQAPGQGLEWMG    WISI--YSGNTDYAQKFQG     RVTMTTDTSRRTAYMELRSLRSDDTAVYYCAR        DGGGAYEDVWSGEYPEYYAMDV      WGQGTTVTVSS
DP-14       ---V--GA------V----K----T--        ---G--    --------------    ---A---N---N---L--      ------TS-----------------------         ----------------------      -----------
```

Figure 4A

```
            FR1                                CDR1        FR2              CDR2                    FR3                                    CDR3                    FR4
                                                                                                                                                                    1   1
         1        2         3                            4                5         6          7         8         9                            1                  0   1
1234567890123456789012345678901234567890  1ab2345  678901234566789  012abc34567890123456   67890123456789012abc3456789012344  567890abcdefghijklmno12  3456789012123
                                                                                                                                                   1
                                                                                                                                                   0

DP-14    QVQLVQSGAEVKKPGASVKVSCKASGYTFT   S--YGIS  WVRQAPGQGLEWMG   WISA--YNGNTNYAQKLQG    RVTMTTDTSTSTAYMELRSLRSDDTAVYYCAR    DGGGAYEDVWSGEYPEYYAMDV   WGQGTTVTVSS
VH IT-2  ----L--AT--------M-------M----P--  ---D--   -----------      ---I---S---D----F--    -----------------------RR---------
VH EL-5  -----L--AT--------M-------M----P--  ---D--   -------V---      ---I---S---D----F--    -----------------------RR---------
VH EL-25 ----L---A---R----------------P--   ---D--   ---------T--     ---I---S---D----F--    ----------------------------------
```

Figure 4B

CDR3

EL-14   QQNGGWYEGPLLEPRPD--ALDI
         ||   ||           |•|•|•
IT-2    DGGGGAYEDVWSGEYPEYYAMDV

Figure 4C

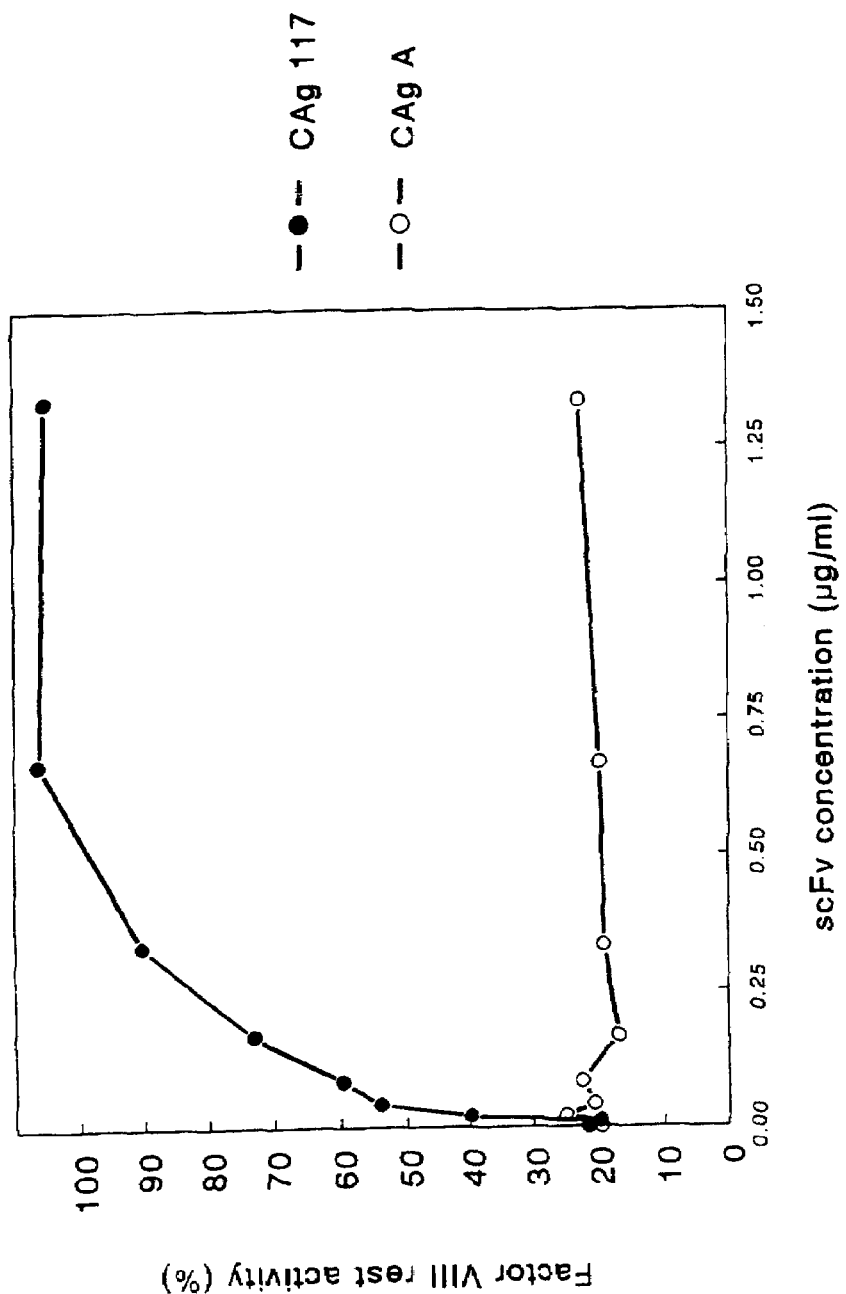
Figure 7A NEUTRALIZATION BY scFv EL-14

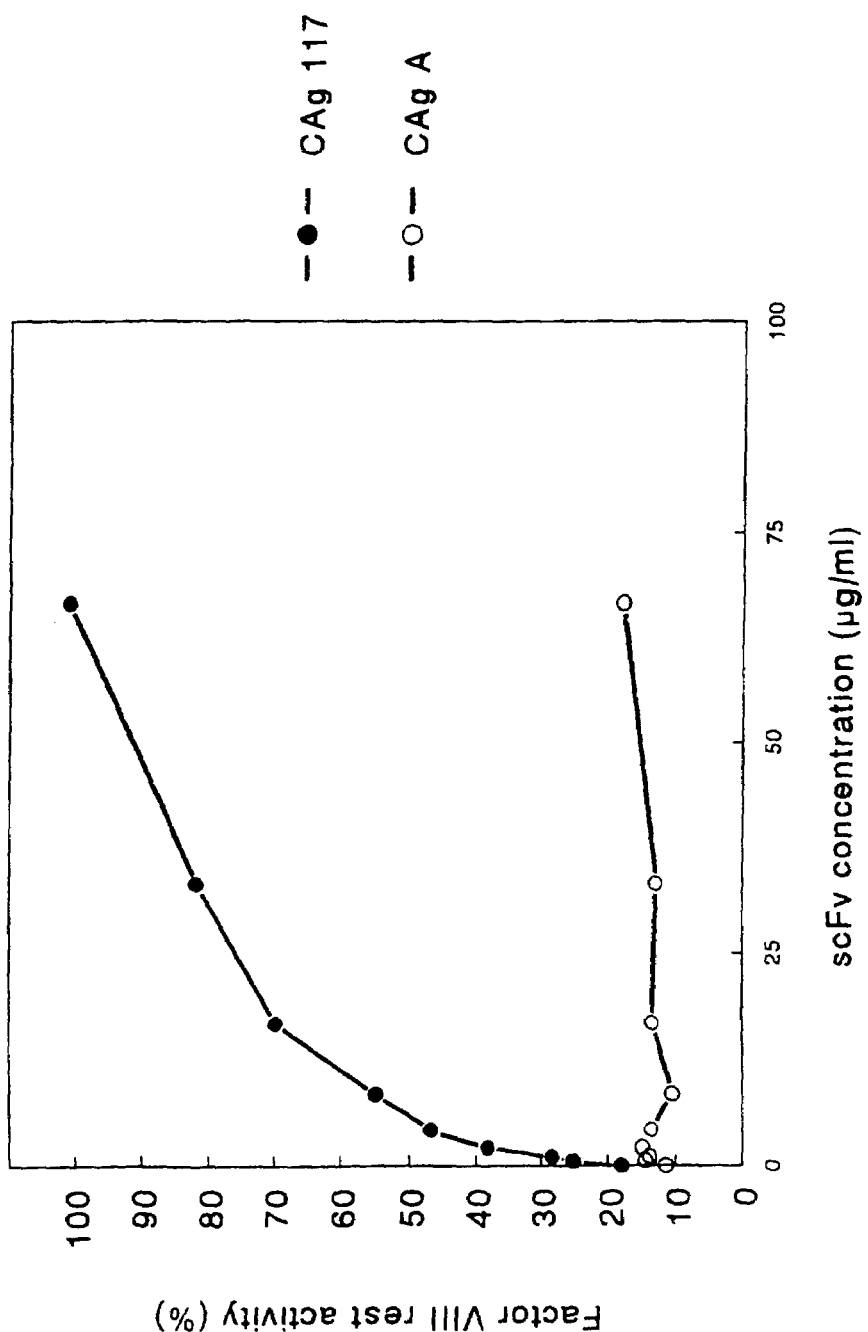
Figure 7B NEUTRALIZATION BY scFv IT-2

Deduced protein sequences of isolated FVIII A3-C1 specific scFv

```
Heavy chains
              FR1                              CDR1        FR2                CDR2               FR3                                    CDR3                           FR4
                                                                                                                                         1                      1   1
          1         2         3                          4         5         6         7         8         9         0                  0                      1   1
  1234567890123456789012345678901234567890  12345  6789012345678 9  012345678901234567890123456 78901234567890123 45  6789012345678901 2abc34567890123  567890abcdefghi12  34567890123

DP-15  QVQLVQSGAEVKKPGASVKVSCKAASGYTFT  SYDIN  WVRQATGQGLEWMG  WMNPNSGNTGYAQKFQG  RVTMTRNTSISTAYMELSSLRSEDTAVYYCAR
B38    ---L-YA-D------------T---I----                       --------A-F----K-    --L-L-D-T-------RN-E-------------    CDITLLIWFGPAPYNDS WGQGTLV

DP-31  EVQLVESGGGLVQPGRSLRLSCAASGFTFD  DYAMH  WVRQAPGKGLEWVS  GISWNSGSIGYADSVKG  RFTISRDNAKNSLYLQMNSLRAEDTALYYCAK  D
B18    Q----Q-----------------L----G    ---I-  ------E------   -VT-SGTT--P------                             ---Y-------  ---L  PYINSSNYRRGVAAFDI WGQGTMVTVSS

DP-49  QVQLVESGGGVVQPGRSLRLSCAASGFTFS  SYGMH  WVRQAPGKGLEWVS  VISYDGSNKYYADSVKG  RFTISRDNSKNTLYLQMNSLRAEDTAVYYCAK
B35    E---------------------VD-L----                       ---A---------    ------ND----                  -A-----A-----TI---------    DLIESNI     AEAL WGQGTLVTVSS

DP-77  EVQLVESGGGLVKPGGSLRLSCAASGFTFS  SYSMN  WVRQAPGKGLEWVS  SISSSSSYIYYADSVKG  RFTISRDNAKNSLYLQMNSLRAEDTAVYYCAR
B04    ---K-E-------------------R-DIH                       -----T-------    ----GGN-D----                  -----N-VV-------M---F---    DGTIFGSAATWR AFDI WGRGTMVTVSSG
```

Figure 9A

```
+1  Gln  Val  Gln  Leu  Leu  Gln  Ser  Ala  Ala  Asp  Val  Lys  Lys  Pro  Gly  Ala  Ser
    CAGGTGCAGC TGTTGCAGTC TGCAGCTGAC GTGAAGAAGC CTGGGGCCTC 50
    GTCCACGTCG ACAACGTCAG ACGTCGACTG CACTTCTTCG GACCCCGGAG

+1       Val  Lys  Val  Ser  Cys  Thr  Ala  Ser  Gly  Tyr  Ile  Phe  Thr  Ser  Tyr  Asp  Ile
    AGTGAAGGTC TCCTGTACGG CTTCTGGATA CATCTTCACC AGTTATGATA 100
    TCACTTCCAG AGGACATGCC GAAGACCTAT GTAGAAGTGG TCAATACTAT

+1       Asn  Trp  Val  Arg  Gln  Ala  Thr  Gly  Gln  Gly  Leu  Glu  Trp  Met  Gly  Trp
    TCAACTGGGT GCGACAGGCC ACTGGACAAG GGCTTGAGTG GATGGGATGG 150
    AGTTGACCCA CGCTGTCCGG TGACCTGTTC CCGAACTCAC CTACCCTACC

+1  Met  Asn  Pro  Asn  Ser  Gly  Asn  Ala  Gly  Phe  Ala  Gln  Lys  Phe  Lys  Gly  Arg
    ATGAATCCTA ACAGTGGTAA CGCAGGCTTT GCACAGAAGT TTAAGGGCAG 200
    TACTTAGGAT TGTCACCATT GCGTCCGAAA CGTGTCTTCA AATTCCCGTC

+1       Leu  Thr  Leu  Thr  Arg  Asp  Thr  Ser  Thr  Ser  Thr  Ala  Tyr  Met  Glu  Leu  Arg
    ACTCACCTTG ACCAGGGACA CTTCCACAAG CACAGCCTAC ATGGAGCTGA 250
    TGAGTGGAAC TGGTCCCTGT GAAGGTGTTC GTGTCGGATG TACCTCGACT

+1       Arg  Leu  Glu  Ser  Glu  Asp  Thr  Ala  Val  Tyr  Tyr  Cys  Ala  Arg  Cys  Asp
    GGAGACTGGA ATCTGAGGAC ACGGCCGTGT ATTACTGTGC GAGATGTGAC 300
    CCTCTGACCT TAGACTCCTG TGCCGGCACA TAATGACACG CTCTACACTG

+1  Thr  Thr  Leu  Leu  Ile  Trp  Phe  Gly  Pro  Ala  Pro  Tyr  Tyr  Asp  Ser  Trp  Gly
    ACCACACTCT TAATCTGGTT CGGGCCCGCC CCTACTATG ACTCCTGGGG 350
    TGGTGTGAGA ATTAGACCAA GCCCGGGCGG GGGATGATAC TGAGGACCCC

+1  Gln  Gly  Thr  Leu  Val
    CCAGGGAACT CTAGTC
    GGTCCCTTGA GATCAG                                              400
```

Figure 9B

```
+1   Gln  Val  Gln  Leu  Val  Gln  Ser  Gly  Gly  Gly    Leu  Val  Gln  Pro  Gly  Lys  Ser
     CAGGTGCAAC TGGTGCAGTC TGGGGGAGGC TTGGTACAGC CTGGCAAGTC  50
     GTCCACGTTG ACCACGTCAG ACCCCCTCCG AACCATGTCG GACCGTTCAG

-1      Leu  Arg  Leu    Ser  Cys  Ala   Ala   Ser  Gly  Phe   Thr  Phe  Gly    Asp  Tyr  Ala  Ile
     CCTGAGACTC TCCTGTGCAG CCTCTGGATT CACATTTGGC GATTATGCCA  100
     GGACTCTGAG AGGACACGTC GGAGACCTAA GTGTAAACCG CTAATACGGT

+1      His  Trp  Val   Arg  Gln  Ala    Pro  Gly  Glu  Gly   Leu  Glu  Trp  Val  Ser  Gly
     TACACTGGGT CCGGCAAGCT CCAGGGGAGG GCCTGGAGTG GGTCTCAGGT  150
     ATGTGACCCA GGCCGTTCGA GGTCCCCTCC CGGACCTCAC CCAGAGTCCA

+:   Val  Thr  Trp  Ser   Gly  Thr  Thr   Ile  Gly  Phe   Ala  Asp  Ser  Val  Lys  Gly  Arg
     GTTACTTGGA GTGGTACTAC TATAGGCTTT GCGGACTCTG TGAAGGGCCG  200
     CAATGAACCT CACCATGATG ATATCCGAAA CGCCTGAGAC ACTTCCCGGC

+:      Phe  Thr  Ile    Ser  Arg  Asp  Asn  Ala  Lys  Asn  Ser  Leu  Tyr   Leu  Tyr  Met  Asn
     ATTCACCATC TCCAGAGACA ACGCCAAGAA TTCCCTGTAT CTGTACATGA  250
     TAAGTGGTAG AGGTCTCTGT TGCGGTTCTT AAGGGACATA GACATGTACT

+1      Ser  Leu  Arg   Ala  Glu  Asp   Thr  Ala  Leu  Tyr  Tyr  Cys   Ala  Leu  Pro  Tyr
     ACAGTCTGAG AGCTGAAGAC ACGGCCTTGT ATTATTGTGC CTTACCATAT  300
     TGTCAGACTC TCGACTTCTG TGCCGGAACA TAATAACACG GAATGGTATA

+:   Ile  Asn  Ser  Ser  Asn  Tyr  Arg  Arg  Gly  Val   Ala  Ala  Phe  Asp  Ile  Trp  Gly
     ATCAACTCGT CCAACTACAG AAGAGGGGTC GCTGCCTTCG ATATCTGGGG  350
     TAGTTGAGCA GGTTGATGTC TTCTCCCCAG CGACGGAAGC TATAGACCCC

+:      Gln  Gly  Thr    Met  Val  Thr   Val  Ser  Ser
     CCAAGGGACA ATGGTCACCG TGTCGAGT                      400
     GGTTCCCTGT TACCAGTGGC ACAGCTCA
```

Figure 9C

```
+1   Glu  Val  Gln  Leu  Val  Glu  Ser  Gly  Gly  Gly       Leu  Val  Gln  Pro  Gly  Arg  Ser
     GAGGTGCAGC TGGTGGAGTC TGGGGGAGGC TTGGTACAGC CTGGGAGGTC 50
     CTCCACGTCG ACCACCTCAG ACCCCCTCCG AACCATGTCG GACCCTCCAG

+1        Leu  Arg  Leu   Ser  Cys  Val  Asp  Ser  Gly  Leu  Thr  Phe  Ser   Ser  Tyr  Gly  Met
     CCTGAGACTC TCCTGTGTAG ACTCTGGACT CACCTTCAGT AGTTATGGCA 100
     GGACTCTGAG AGGACACATC TGAGACCTGA GTGGAAGTCA TCAATACCGT

+1        His  Trp  Val  Arg  Gln  Ala   Pro  Gly  Ala  Gly  Leu  Glu  Trp  Val  Ala  Val
     TGCACTGGGT CCGCCAGGCT CCAGGCGCGG GGCTGGAGTG GGTGGCCGTT 150
     ACGTGACCCA GGCGGTCCGA GGTCCGCGCC CCGACCTCAC CCACCGGCAA

-1   Ile  Ser  Tyr  Asp  Gly  Asn  Asp  Lys  Tyr  Tyr   Ala  Asp  Ser  Val  Lys  Gly  Arg
     ATTTCATACG ACGGAAATGA TAAATATTAT GCAGACTCCG TGAAGGGCCG 200
     TAAAGTATGC TGCCTTTACT ATTTATAATA CGTCTGAGGC ACTTCCCGGC

+1    Phe  Ala  Ile   Ser  Arg  Asp  Asn  Ala  Lys  Asn  Thr  Leu  Tyr   Leu  Gln  Met  Asn
     ATTCGCCATC TCCAGAGACA ATGCCAAGAA CACGCTGTAT CTGCAAATGA 250
     TAAGCGGTAG AGGTCTCTGT TACGGTTCTT GTGCGACATA GACGTTTACT

+1       Ser  Leu  Thr  Ile  Glu  Asp   Thr  Ala  Val  Tyr  Tyr  Cys  Ala  Lys  Asp  Leu
     ACAGCCTGAC AATAGAGGAC ACGGCTGTCT ATTATTGTGC GAAAGATCTC 300
     TGTCGGACTG TTATCTCCTG TGCCGACAGA TAATAACACG CTTTCTAGAG

+1   Ile  Glu  Ser  Asn  Ile  Ala  Glu  Ala  Leu  Trp   Gly  Gln  Gly  Thr  Leu  Val  Thr
     ATAGAATCAA ATATTGCGGA GGCCCTCTGG GGCCAGGGAA CCCTGGTCAC 350
     TATCTTAGTT TATAACGCCT CCGGGAGACC CCGGTCCCTT GGGACCAGTG

+1        Val  Ser  Ser
     CGTGTCGAGT                                              400
     GCACAGCTCA
```

Figure 9D

```
     ┌Glu┐ ┌Val┐ ┌Gln┐ ┌─Leu─┐ ┌Val┐ ┌Lys┐ ┌─Ser─┐ ┌Gly┐ ┌Glu┐ ┌Gly┐   ┌Leu┐ ┌Val┐ ┌Lys┐ ┌─Pro─┐ ┌Gly┐ ┌Gly┐ ┌Ser─
+1   GAGGTGCAGC TGGTGAAGTC TGGGGAAGGC CTGGTCAAGC CTGGGGGGTC   50
     CTCCACGTCG ACCACTTCAG ACCCCTTCCG GACCAGTTCG GACCCCCCAG

┐ ┌Leu┐ ┌Arg┐ ┌Leu┐ ┌Ser┐ ┌Cys┐ ┌Ala┐ ┌─Ala─┐ ┌Ser┐ ┌Gly┐ ┌─Phe─┐ ┌Thr┐ ┌Phe┐ ┌Arg┐   ┌Arg┐ ┌Tyr┐ ┌Asp┐ ┌Ile─
-1   CCTGAGACTC TCCTGTGCAG CCTCTGGATT CACCTTCAGG AGATATGATA  100
     GGACTCTGAG AGGACACGTC GGAGACCTAA GTGGAAGTCC TCTATACTAT

┐   ┌His┐ ┌Trp┐ ┌─Val─┐ ┌Arg┐ ┌Gln┐ ┌Thr┐   ┌Pro┐ ┌Gly┐ ┌Lys┐ ┌─Gly─┐ ┌Leu┐ ┌Glu┐ ┌─Trp─┐ ┌Val┐ ┌Ser┐ ┌Ser┐
+1   TCCACTGGGT CCGCCAGACT CCAGGGAAGG GCCTGGAGTG GGTCTCATCC  150
     AGGTGACCCA GGCGGTCTGA GGTCCCTTCC CGGACCTCAC CCAGAGTAGG

┌Ile┐ ┌Ser┐ ┌Ser┐ ┌─Gly─┐ ┌Gly┐ ┌Asn┐ ┌─Tyr─┐ ┌Ile┐ ┌Asp┐ ┌Tyr┐   ┌Ala┐ ┌Asp┐ ┌Ser┐ ┌─Val─┐ ┌Lys┐ ┌Gly┐ ┌Arg─
+1   ATCAGTAGTG GTGGTAATTA CATAGACTAC GCAGACTCTG TGAAGGGCCG  200
     TAGTCATCAC CACCATTAAT GTATCTGATG CGTCTGAGAC ACTTCCCGGC

┐   ┌Phe┐ ┌Thr┐ ┌Ile┐ ┌Ser┐ ┌Arg┐ ┌Asp┐ ┌─Asn─┐ ┌Ala┐ ┌Asn┐ ┌─Asn─┐ ┌Val┐ ┌Val┐ ┌Tyr┐ ┌Leu┐ ┌Gln┐ ┌Met┐ Asn
+1   ATTCACCATC TCCAGAGACA ACGCCAACAA TGTTGTCTAT CTACAAATGA  250
     TAAGTGGTAG AGGTCTCTGT TGCGGTTGTT ACAACAGATA GATGTTTACT

┐   ┌Ser┐ ┌Leu┐ ┌─Arg─┐ ┌Ala┐ ┌Glu┐ ┌Asp┐ ┌Met┐ ┌Ala┐ ┌Val┐ ┌─Tyr─┐ ┌Phe┐ ┌Cys┐ ┌Ala┐ ┌Arg┐ ┌Asp┐ ┌Gly┐
+1   ACAGCCTGAG AGCCGAGGAC ATGGCTGTCT ATTTCTGTGC GAGAGATGGG  300
     TGTCGGACTC TCGGCTCCTG TACCGACAGA TAAAGACACG CTCTCTACCC

┌Thr┐ ┌Ile┐ ┌Phe┐ ┌─Gly─┐ ┌Ser┐ ┌Ala┐ ┌─Ala─┐ ┌Thr┐ ┌Trp┐ ┌Arg┐   ┌Ala┐ ┌Phe┐ ┌Asp┐ ┌─Ile─┐ ┌Trp┐ ┌Gly┐ ┌Arg─
-1   ACGATTTTTG GATCGGCGGC GACCTGGCGG GCTTTTGATA TCTGGGGCCG  350
     TGCTAAAAAC CTAGCCGCCG CTGGACCGCC CGAAAACTAT AGACCCCGGC

┐   ┌Gly┐ ┌Thr┐ ┌Met┐ ┌─Val─┐ ┌Thr┐ ┌Val┐ ┌─Ser─┐ ┌Ser┐
-1   GGGGACAATG GTCACCGTGT CGAGT                              400
     CCCCTGTTAC CAGTGGCACA GCTCA
```

Figure 9E

Deduced protein sequences of isolated FVIII A2 specific scFv

Heavy chains

```
              FR1                              CDR1          FR2                CDR2                         FR3                                          CDR3                  FR4
         1         2         3            4           5          6         7         8         9          1   1                        1   1
1234567890123456789012345678901234567890  12345 6789012345678901 2a3456789012345 67890123456789012abc34567890123 4 567890abcde12 34567890123
DP-10    QVQLVQSGAEVKKPGSSVKVSCKASGGTFS   SYAIS WVRQAPGQGLEWMG  QIIPIFGTANYAQKFQG RVTITADESTSTAYMELSSLRSEDTAVYYCAR EL DWFYI         WGQGTMVTVSS
         ----------------H--              -H--- --------------- D----L--G------- ---------------T-T--------------

DP-47    EVQLLESGGGLVQPGGSLRLSCAASGFTFS   SYAMS WVRQAPGKGLEWVS  AISGSGGSTYYADSVKG RFTISRDNSKNTLYLQMNSLRAEDTAVYYCAK   RGRGGYKYYGMDV WGQGTTVTVSS
         ---V----D--------                -NF-- ------------A-- --G-RS-T-P------- ------------V--E--------I------
```

Figure 11A

```
     ┌Gln┐ ┌Val┐ ┌Gln┐ ┌─Leu─┐ ┌Val┐ ┌Gln┐ ┌─Ser─┐ ┌Gly┐ ┌Ala┐ ┌Glu┐    ┌Val┐ ┌Lys┐ ┌Lys┐ ┌─Pro─┐ ┌Gly┐ ┌Ser┐ ─Ser─
+1   CAGGTGCAGC TGGTGCAGTC TGGGGCTGAG GTGAAGAAGC CTGGGTCCTC    50
     GTCCACGTCG ACCACGTCAG ACCCCGACTC CACTTCTTCG GACCCAGGAG

┌Val┐ ┌Lys┐ ┌Val┐ ┌Ser┐ ┌Cys┐ ┌Lys┐ ┌─Ala─┐ ┌Ser┐ ┌Gly┐ ┌─Gly─┐ ┌Thr┐ ┌Phe┐ ┌Ser┐    ┌Ser┐ ┌His┐ ┌Ala┐ ┌Ile
+1   GGTGAAGGTC TCCTGCAAGG CTTCTGGAGG CACCTTCAGC AGTCATGCTA   100
     CCACTTCCAG AGGACGTTCC GAAGACCTCC GTGGAAGTCG TCAGTACGAT

─Ser─ ┌Trp┐ ─Val─ ┌Arg┐ ┌Gln┐ ┌Ala┐    ┌Pro┐ ┌Gly┐ ┌Gln┐ ┌─Gly─┐ ┌Leu┐ ┌Glu┐ ┌─Trp─┐ ┌Met┐ ┌Gly┐ ┌Asp┐
+1   TCAGCTGGGT GCGACAGGCC CCTGGACAAG GGCTTGAGTG GATGGGAGAC   150
     AGTCGACCCA CGCTGTCCGG GGACCTGTTC CCGAACTCAC CTACCCTCTG

─Ile─ ─Ile─ ┌Pro┐ ─Ile─ ┌Leu┐ ┌Gly┐ ┌─Thr─┐ ┌Gly┐ ┌Asn┐ ┌Tyr┐    ┌Ala┐ ┌Gln┐ ┌Lys┐ ┌─Phe─┐ ┌Gln┐ ┌Gly┐ ┌Arg─
+1   ATCATCCCTA TCCTTGGTAC AGGAAACTAC GCACAGAAGT TCCAGGGCAG   200
     TAGTAGGGAT AGGAACCATG TCCTTTGATG CGTGTCTTCA AGGTCCCGTC

┌Val┐ ┌Thr┐ ┌Ile┐    ┌Thr┐ ┌Ala┐ ┌Asp┐ ┌─Glu─┐ ┌Ser┐ ┌Thr┐ ┌─Ser─┐ ┌Thr┐ ┌Ala┐ ┌Tyr┐    ┌Met┐ ┌Glu┐ ┌Leu┐ ┌Ser
+1   AGTCACGATT ACCGCGGACG AGTCCACGAG CACAGCCTAC ATGGAGCTGA   250
     TCAGTGCTAA TGGCGCCTGC TCAGGTGCTC GTGTCGGATG TACCTCGACT

┌Thr┐ ┌Leu┐ ┌─Thr─┐ ┌Ser┐ ┌Glu┐ ┌Asp┐    ┌Thr┐ ┌Ala┐ ┌Val┐ ┌─Tyr─┐ ┌Tyr┐ ┌Cys┐ ┌─Glu─┐ ┌Leu┐ ┌Asp┐ ┌Trp┐
+1   GCACCCTGAC ATCTGAGGAC ACGGCCGTGT ATTACTGTGA ACTTGACTGG   300
     CGTGGGACTG TAGACTCCTG TGCCGGCACA TAATGACACT TGAACTGACC

┌Phe┐ ─Tyr─ ─Ile─ ─Trp─ ┌Gly┐ ┌Gln┐ ─Gly─ ┌Thr┐ ┌Met┐ ┌Val┐    ┌Thr┐ ┌Val┐ ┌Ser┐ ┌─Ser─┐
     TTCTATATCT GGGGCCAAGG GACAATGGTC ACCGTGTCGA GT            350
     AAGATATAGA CCCCGGTTCC CTGTTACCAG TGGCACAGCT CA
```

Figure 11B

```
+1   Glu  Val  Gln  Leu  Val  Glu  Ser  Gly  Gly  Asp   Leu  Val  Gln  Pro  Gly  Gly  Ser-
     GAGGTGCAGC TGGTGGAGTC TGGGGGAGAC TTGGTACAGC CTGGGGGGTC 50
     CTCCACGTCG ACCACCTCAG ACCCCCTCTG AACCATGTCG GACCCCCCAG

+1    Leu  Arg  Leu   Ser  Cys  Ala   Ala  Ser  Gly  Phe  Thr  Phe  Ser   Asn  Phe  Ala  Met
     CCTGAGACTC TCCTGTGCAG CCTCTGGATT CACCTTTAGC AACTTTGCCA 100
     GGACTCTGAG AGGACACGTC GGAGACCTAA GTGGAAATCG TTGAAACGGT

+1    Ser  Trp  Val  Arg  Gln  Ala   Pro  Gly  Lys  Gly  Leu  Glu  Trp  Val  Ala  Ala
     TGAGCTGGGT CCGCCAGGCT CCCGGGAAGG GGCTGGAGTG GGTCGCGGCT 150
     ACTCGACCCA GGCGGTCCGA GGGCCCTTCC CCGACCTCAC CCAGCGCCGA

+1   Ile  Gly  Gly  Arg  Ser  Gly  Thr  Thr  Phe  Tyr   Ala  Asp  Ser  Val  Lys  Gly  Arg-
     ATTGGCGGTA GAAGTGGTAC CACATTCTAC GCGGACTCCG TGAAGGGCCG 200
     TAACCGCCAT CTTCACCATG GTGTAAGATG CGCCTGAGGC ACTTCCCGGC

+1    Phe  Thr  Ile   Ser  Arg  Asp  Asn  Ser  Lys  Asn  Thr  Val  Tyr   Leu  Glu  Met  Asn
     GTTCACCATC TCCAGAGACA ATTCCAAGAA CACGGTCTAT CTGGAAATGA 250
     CAAGTGGTAG AGGTCTCTGT TAAGGTTCTT GTGCCAGATA GACCTTTACT

+1    Ser  Leu  Arg  Ala  Glu  Asp   Thr  Ala  Ile  Tyr  Tyr  Cys  Ala  Lys  Arg  Gly
     ACAGTCTGAG AGCCGAGGAC ACAGCCATTT ATTACTGTGC GAAAAGAGGG 300
     TGTCAGACTC TCGGCTCCTG TGTCGGTAAA TAATGACACG CTTTTCTCCC

+1   Arg  Gly  Gly  Tyr  Lys  Tyr  Tyr  Gly  Met  Asp   Val  Trp  Gly  Gln  Gly  Thr  Thr-
     CGCGGGGGGT ATAAGTATTA TGGGATGGAC GTCTGGGGCC AGGGGACCAC 350
     GCGCCCCCCA TATTCATAAT ACCCTACCTG CAGACCCCGG TCCCCTGGTG

+1    Val  Thr  Val   Ser  Ser
     GGTCACCGTG TCGAGT                                      400
     CCAGTGGCAC AGCTCA
```

Figure 11C

SEQUENCE LISTING

<160> NUMBER OF SEQ ID NOS: 55

<210> SEQ ID NO 1
<211> LENGTH: 24
<212> TYPE: DNA
<213> ORGANISM: Homo sapiens

<400> SEQUENCE: 1
cttgtccacc ttggtgttgc tggg        24

<210> SEQ ID NO 2
<211> LENGTH: 21
<212> TYPE: DNA
<213> ORGANISM: Homo sapiens

<400> SEQUENCE: 2
acgttgcagg tgtaggtctt c        21

<210> SEQ ID NO 3
<211> LENGTH: 23
<212> TYPE: DNA
<213> ORGANISM: Homo sapiens

<400> SEQUENCE: 3
caggtgcagc tggtgcagtc tgg        23

<210> SEQ ID NO 4

```
<211> LENGTH: 23
<212> TYPE: DNA
<213> ORGANISM: Homo sapiens

<400> SEQUENCE: 4
caggtcaact taagggagtc tgg                                              23

<210> SEQ ID NO 5
<211> LENGTH: 23
<212> TYPE: DNA
<213> ORGANISM: Homo sapiens

<400> SEQUENCE: 5
gaggtgcagc tggtggagtc tgg                                              23

<210> SEQ ID NO 6
<211> LENGTH: 23
<212> TYPE: DNA
<213> ORGANISM: Homo sapiens

<400> SEQUENCE: 6
gaggtgcagc tgttgcagtc ggg                                              23

<210> SEQ ID NO 7
<211> LENGTH: 23
<212> TYPE: DNA
<213> ORGANISM: Homo sapiens

<400> SEQUENCE: 7
gaggtacagc tgcagcagtc tgc                                              23

<210> SEQ ID NO 8
<211> LENGTH: 23
<212> TYPE: DNA
<213> ORGANISM: Homo sapiens

<400> SEQUENCE: 8
caggtacagc tgcagcagtc agg                                              23

<210> SEQ ID NO 9
<211> LENGTH: 36
<212> TYPE: DNA
<213> ORGANISM: Homo sapiens

<400> SEQUENCE: 9
gagtcattct cgtgtcgaca cggtgaccag ggtgcc                                36

<210> SEQ ID NO 10
<211> LENGTH: 36
<212> TYPE: DNA
<213> ORGANISM: Homo sapiens

<400> SEQUENCE: 10
gagtcattct cgtgtcgaca cggtgaccat tgtccc                                36

<210> SEQ ID NO 11
<211> LENGTH: 36
<212> TYPE: DNA
<213> ORGANISM: Homo sapiens

<400> SEQUENCE: 11
gagtcattct cgtgtcgaca cggtgaccag ggttcc                                36
```

```
<210> SEQ ID NO 12
<211> LENGTH: 36
<212> TYPE: DNA
<213> ORGANISM: Homo sapiens

<400> SEQUENCE: 12
gagtcattct cgtgtcgaca cggtgaccgt ggtccc                          36

<210> SEQ ID NO 13
<211> LENGTH: 28
<212> TYPE: DNA
<213> ORGANISM: Homo sapiens

<400> SEQUENCE: 13
aatccatggc ccaggtgcag ctggtgca                                   28

<210> SEQ ID NO 14
<211> LENGTH: 28
<212> TYPE: DNA
<213> ORGANISM: Homo sapiens

<400> SEQUENCE: 14
aatccatggc ccaggtcaac ttaaggga                                   28

<210> SEQ ID NO 15
<211> LENGTH: 28
<212> TYPE: DNA
<213> ORGANISM: Homo sapiens

<400> SEQUENCE: 15
aatccatggc cgaggtgcag ctggtgga                                   28

<210> SEQ ID NO 16
<211> LENGTH: 28
<212> TYPE: DNA
<213> ORGANISM: Homo sapiens

<400> SEQUENCE: 16
aatccatggc cgaggtgcag ctgttgca                                   28

<210> SEQ ID NO 17
<211> LENGTH: 28
<212> TYPE: DNA
<213> ORGANISM: Homo sapiens

<400> SEQUENCE: 17
aatccatggc cgaggtacag ctgcagca                                   28

<210> SEQ ID NO 18
<211> LENGTH: 28
<212> TYPE: DNA
<213> ORGANISM: Homo sapiens

<400> SEQUENCE: 18
aatccatggc ccaggtacag ctgcagca                                   28

<210> SEQ ID NO 19
<211> LENGTH: 390
<212> TYPE: DNA
<213> ORGANISM: Homo sapiens

<400> SEQUENCE: 19
caggtgcagc tggtgcagtc tggggctgag gcgaagaagc ctgggtcctc ggtgaaggtc    60
```

```
tcctgcaagg cttctggaga caccttcaac agctttccta tcagttgggt gcgacaggcc    120
cctggacaag ggcttgagtg gatgggaggg atcatcccta tctttggttc aacaaagtac    180
gcacagaagt tccagggcag agtcacgatg accgcggacg gatccacgag tacagcctac    240
atggaactga acagcctgag atctgaggac acggccatat attactgtgc gcgacaacag    300
aacggcggct ggtacgaagg accgttgctt gagccgaggc ctgatgctct tgatatctgg    360
ggccaaggga caatggtcac cgtgtcgagt                                     390
```

```
<210> SEQ ID NO 20
<211> LENGTH: 296
<212> TYPE: DNA
<213> ORGANISM: Homo sapiens

<400> SEQUENCE: 20
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaga        296
```

```
<210> SEQ ID NO 21
<211> LENGTH: 396
<212> TYPE: DNA
<213> ORGANISM: Homo sapiens

<400> SEQUENCE: 21
caggtgcagc tgttgcagtc tgcaactgag gtgaaaaagc ctggggcctc aatgaaggtc     60
tcctgcatgg cttctggtta ccccttacc agctatgata tcagttgggt gcgacaggcc    120
cctggacaag ggcttgagtg gatgggatgg atcagcattt atagtggtaa cacagactat    180
gcacagaagt tccagggcag agtcaccatg acgacagaca catccaggag aacagcctac    240
atggagctga ggagcctgag atctgacgac acggccgtct attattgtgc gagagatggg    300
ggggggggtg cctatgaaga tgttttggagt ggtgagtacc ccgaatacta cgctatggac    360
gtctggggcc aagggaccac ggtcaccgtg tcgagt                              396
```

```
<210> SEQ ID NO 22
<211> LENGTH: 296
<212> TYPE: DNA
<213> ORGANISM: Homo sapiens

<400> SEQUENCE: 22
caggttcagc tggtgcagtc tggagctgag gtgaagaagc ctggggcctc agtgaaggtc     60
tcctgcaagg cttctggtta caccttacc agctatggta tcagctgggt gcgacaggcc    120
cctggacaag ggcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggccgtgt attactgtgc gagaga        296
```

```
<210> SEQ ID NO 23
<211> LENGTH: 130
<212> TYPE: PRT
<213> ORGANISM: Homo sapiens

<400> SEQUENCE: 23

Gln Val Gln Leu Val Gln Ser Gly Ala Glu Ala Lys Lys Pro Gly Ser
```

```
                1               5                   10                  15
        Ser Val Lys Val Ser Cys Lys Ala Ser Gly Asp Thr Phe Asn Ser Phe
                        20                  25                  30

Pro Ile Ser Trp Val Arg Gln Ala Pro Gly Gln Gly Leu Glu Trp Met
                    35                  40                  45

Gly Gly Ile Ile Pro Ile Phe Gly Ser Thr Lys Tyr Ala Gln Lys Phe
                50                  55                  60

Gln Gly Arg Val Thr Met Thr Ala Asp Gly Ser Thr Ser Thr Ala Tyr
        65                  70                  75                  80

Met Glu Leu Asn Ser Leu Arg Ser Glu Asp Thr Ala Ile Tyr Tyr Cys
                        85                  90                  95

Ala Arg Gln Gln Asn Gly Gly Trp Tyr Glu Gly Pro Leu Leu Glu Pro
                        100                 105                 110

Arg Pro Asp Ala Leu Asp Ile Trp Gly Gln Gly Thr Met Val Thr Val
                    115                 120                 125

Ser Ser
            130

<210> SEQ ID NO 24
<211> LENGTH: 98
<212> TYPE: PRT
<213> ORGANISM: Homo sapiens

<400> SEQUENCE: 24

Gln Val Gln Leu Val Gln Ser Gly Ala Glu Val Lys Lys Pro Gly Ser
        1               5                   10                  15

Ser Val Lys Val Ser Cys Lys Ala Ser Gly Gly Thr Phe Ser Ser Tyr
                        20                  25                  30

Ala Ile Ser Trp Val Arg Gln Ala Pro Gly Gln Gly Leu Glu Trp Met
                    35                  40                  45

Gly Gly Ile Ile Pro Ile Phe Gly Thr Ala Asn Tyr Ala Gln Lys Phe
                50                  55                  60

Gln Gly Arg Val Thr Ile Thr Ala Asp Glu Ser Thr Ser Thr Ala Tyr
        65                  70                  75                  80

Met Glu Leu Ser Ser Leu Arg Ser Glu Asp Thr Ala Val Tyr Tyr Cys
                        85                  90                  95

Ala Arg

<210> SEQ ID NO 25
<211> LENGTH: 132
<212> TYPE: PRT
<213> ORGANISM: Homo sapiens

<400> SEQUENCE: 25

Gln Val Gln Leu Leu Gln Ser Ala Thr Glu Val Lys Lys Pro Gly Ala
        1               5                   10                  15

Ser Met Lys Val Ser Cys Met Ala Ser Gly Tyr Pro Phe Thr Ser Tyr
                        20                  25                  30

Asp Ile Ser Trp Val Arg Gln Ala Pro Gly Gln Gly Leu Glu Trp Met
                    35                  40                  45

Gly Trp Ile Ser Ile Tyr Ser Gly Asn Thr Asp Tyr Ala Gln Lys Phe
                50                  55                  60

Gln Gly Arg Val Thr Met Thr Thr Asp Thr Ser Arg Arg Thr Ala Tyr
        65                  70                  75                  80

Met Glu Leu Arg Ser Leu Arg Ser Asp Asp Thr Ala Val Tyr Tyr Cys
                        85                  90                  95
```

-continued

Ala Arg Asp Gly Gly Gly Gly Ala Tyr Glu Asp Val Trp Ser Gly Glu
            100                 105                 110

Tyr Pro Glu Tyr Tyr Ala Met Asp Val Trp Gly Gln Gly Thr Thr Val
            115                 120                 125

Thr Val Ser Ser
        130

<210> SEQ ID NO 26
<211> LENGTH: 98
<212> TYPE: PRT
<213> ORGANISM: Homo sapiens

<400> SEQUENCE: 26

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 27
<211> LENGTH: 98
<212> TYPE: PRT
<213> ORGANISM: Homo sapiens

<400> SEQUENCE: 27

Gln Val Gln Leu Leu Gln Ser Ala Thr Glu Val Lys Lys Pro Gly Ala
1               5                   10                  15

Ser Met Lys Val Ser Cys Met Ala Ser Gly Tyr Pro Phe Thr Ser Tyr
            20                  25                  30

Asp Ile Ser Trp Val Arg Gln Ala Pro Gly Gln Gly Leu Glu Trp Val
        35                  40                  45

Gly Trp Ile Ser Ala Tyr Asn Gly Asn Thr His Tyr Ala Gln Lys Phe
    50                  55                  60

Gln Gly Arg Val Thr Met Thr Thr Asp Thr Ser Arg Arg Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 28
<211> LENGTH: 98
<212> TYPE: PRT
<213> ORGANISM: Homo sapiens

<400> SEQUENCE: 28

Gln Val Gln Leu Leu Gln Ser Ala Ala Glu Val Arg Lys Pro Gly Ala
1               5                   10                  15

Ser Val Lys Val Ser Cys Lys Ala Ser Gly Tyr Pro Phe Thr Ser Tyr
            20                  25                  30

```
Asp Ile Ser Trp Val Arg Gln Ala Pro Gly Gln Gly Leu Glu Trp Met
            35                  40                  45

Gly Trp Ile Ser Ile Tyr Ser Gly Asn Thr Asp Tyr Ala Gln Lys Phe
        50                  55                  60

Gln Gly Arg Val Thr Met Thr Thr Asp Thr Ser Arg Arg Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 29
<211> LENGTH: 21
<212> TYPE: PRT
<213> ORGANISM: Homo sapiens

<400> SEQUENCE: 29

Gln Gln Asn Gly Gly Trp Tyr Glu Gly Pro Leu Leu Glu Pro Arg Pro
1               5                   10                  15

Asp Ala Leu Asp Ile
            20

<210> SEQ ID NO 30
<211> LENGTH: 23
<212> TYPE: PRT
<213> ORGANISM: Homo sapiens

<400> SEQUENCE: 30

Asp Gly Gly Gly Gly Ala Tyr Glu Asp Val Trp Ser Gly Glu Tyr Pro
1               5                   10                  15

Glu Tyr Tyr Ala Met Asp Val
            20

<210> SEQ ID NO 31
<211> LENGTH: 98
<212> TYPE: PRT
<213> ORGANISM: Homo sapiens

<400> SEQUENCE: 31

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
        50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 32
<211> LENGTH: 122
<212> TYPE: PRT
<213> ORGANISM: Homo sapiens

<400> SEQUENCE: 32
```

```
Gln Val Gln Leu Leu Gln Tyr Ala Ala Asp Val Lys Lys Pro Gly Ala
1               5                   10                  15

Ser Val Lys Val Ser Cys Thr Ala Ser Gly Tyr Ile Phe Thr Ser Tyr
            20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Ala Gly Phe Ala Gln Lys Phe
50                  55                  60

Lys Gly Arg Leu Thr Leu Thr Arg Asp Thr Ser Thr Ser Thr Ala Tyr
65                  70                  75                  80

Met Glu Leu Arg Asn Leu Glu Ser Glu Asp Thr Ala Val Tyr Tyr Cys
                85                  90                  95

Ala Arg Cys Asp Thr Thr Leu Leu Ile Trp Phe Gly Pro Ala Pro Tyr
                100                 105                 110

Asn Asp Ser Trp Gly Gln Gly Thr Leu Val
            115                 120
```

<210> SEQ ID NO 33
<211> LENGTH: 99
<212> TYPE: PRT
<213> ORGANISM: Homo sapiens

<400> SEQUENCE: 33

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp
```

<210> SEQ ID NO 34
<211> LENGTH: 126
<212> TYPE: PRT
<213> ORGANISM: Homo sapiens

<400> SEQUENCE: 34

```
Gln Val Gln Leu Val Glu Ser Gly Gly Gly Leu Val Gln Pro Gly Lys
1               5                   10                  15

Ser Leu Arg Leu Ser Cys Ala Ala Ser Gly Phe Thr Phe Gly Asp Tyr
            20                  25                  30

Ala Ile His Trp Val Arg Gln Ala Pro Gly Glu Gly Leu Glu Trp Val
            35                  40                  45

Ser Gly Val Thr Trp Ser Gly Thr Ile Gly Phe Ala Asp Ser Val
50                  55                  60

Lys Gly Arg Phe Thr Ile Ser Arg Asp Asn Ala Lys Asn Ser Leu Tyr
65                  70                  75                  80

Leu Tyr Met Asn Ser Leu Arg Ala Glu Asp Thr Ala Leu Tyr Tyr Cys
                85                  90                  95

Ala Leu Pro Tyr Ile Asn Ser Ser Asn Tyr Arg Arg Gly Val Ala Ala
```

```
                100                 105                 110
Phe Asp Ile Trp Gly Gln Gly Thr Met Val Thr Val Ser Ser
        115                 120                 125

<210> SEQ ID NO 35
<211> LENGTH: 98
<212> TYPE: PRT
<213> ORGANISM: Homo sapiens

<400> SEQUENCE: 35

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 36
<211> LENGTH: 120
<212> TYPE: PRT
<213> ORGANISM: Homo sapiens

<400> SEQUENCE: 36

Glu Val Gln Leu Val Glu Ser Gly Gly Gly Leu Val Gln Pro Gly Arg
1               5                   10                  15

Ser Leu Arg Leu Ser Cys Val Asp Ser Gly Leu Thr Phe Ser Ser Tyr
            20                  25                  30

Gly Met His Trp Val Arg Gln Ala Pro Gly Ala Gly Leu Glu Trp Val
        35                  40                  45

Ala Val Ile Ser Tyr Asp Gly Asn Asp Lys Tyr Tyr Ala Asp Ser Val
    50                  55                  60

Lys Gly Arg Phe Ala Ile Ser Arg Asp Asn Ala Lys Asn Thr Leu Tyr
65                  70                  75                  80

Leu Gln Met Asn Ser Leu Thr Ile Glu Asp Thr Ala Val Tyr Tyr Cys
                85                  90                  95

Ala Lys Asp Leu Ile Glu Ser Asn Ile Ala Glu Ala Leu Trp Gly Gln
                100                 105                 110

Gly Thr Leu Val Thr Val Ser Ser
        115                 120

<210> SEQ ID NO 37
<211> LENGTH: 98
<212> TYPE: PRT
<213> ORGANISM: Homo sapiens

<400> SEQUENCE: 37

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

```
Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 38
<211> LENGTH: 126
<212> TYPE: PRT
<213> ORGANISM: Homo sapiens

<400> SEQUENCE: 38

Glu Val Gln Leu Val Lys Ser Gly Glu Gly Leu Val Lys Pro Gly Gly
1               5                   10                  15

Ser Leu Arg Leu Ser Cys Ala Ala Ser Gly Phe Thr Phe Arg Arg Tyr
                20                  25                  30

Asp Ile His Trp Val Arg Gln Thr Pro Gly Lys Gly Leu Glu Trp Val
        35                  40                  45

Ser Ser Ile Ser Ser Gly Gly Asn Tyr Ile Asp Tyr Ala Asp Ser Val
    50                  55                  60

Lys Gly Arg Phe Thr Ile Ser Arg Asp Asn Ala Asn Asn Val Val Tyr
65                  70                  75                  80

Leu Gln Met Asn Ser Leu Arg Ala Glu Asp Met Ala Val Tyr Phe Cys
                85                  90                  95

Ala Arg Asp Gly Thr Ile Phe Gly Ser Ala Ala Thr Trp Arg Ala Phe
                100                 105                 110

Asp Ile Trp Gly Arg Gly Thr Met Val Thr Val Ser Ser Gly
        115                 120                 125

<210> SEQ ID NO 39
<211> LENGTH: 366
<212> TYPE: DNA
<213> ORGANISM: Homo sapiens

<400> SEQUENCE: 39
caggtgcagc tgtttgcagtc tgcagctgac gtgaagaagc ctggggcctc agtgaaggtc      60
tcctgtacgg cttctggata catcttcacc agttatgata tcaactgggt gcgacaggcc     120
actggacaag gcttgagtg gatgggatgg atgaatccta acagtggtaa cgcaggcttt      180
gcacagaagt ttaagggcag actcaccttg accaggaca cttccacaag cacagcctac      240
atggagctga ggagactgga atctgaggac acggccgtgt attactgtgc gagatgtgac      300
accacactct taatctggtt cgggcccgcc ccctactatg actcctgggg ccagggaact      360
ctagtc                                                                 366

<210> SEQ ID NO 40
<211> LENGTH: 122
<212> TYPE: PRT
<213> ORGANISM: Homo sapiens

<400> SEQUENCE: 40

Gln Val Gln Leu Leu Gln Ser Ala Ala Asp Val Lys Lys Pro Gly Ala
1               5                   10                  15
```

-continued

```
Ser Val Lys Val Ser Cys Thr Ala Ser Gly Tyr Ile Phe Thr Ser Tyr
             20                  25                  30
Asp Ile Asn Trp Val Arg Gln Ala Thr Gly Gln Gly Leu Glu Trp Met
         35                  40                  45
Gly Trp Met Asn Pro Asn Ser Gly Asn Ala Gly Phe Ala Gln Lys Phe
     50                  55                  60
Lys Gly Arg Leu Thr Leu Thr Arg Asp Thr Ser Thr Ser Thr Ala Tyr
 65                  70                  75                  80
Met Glu Leu Arg Arg Leu Glu Ser Glu Asp Thr Ala Val Tyr Tyr Cys
                 85                  90                  95
Ala Arg Cys Asp Thr Thr Leu Leu Ile Trp Phe Gly Pro Ala Pro Tyr
            100                 105                 110
Tyr Asp Ser Trp Gly Gln Gly Thr Leu Val
        115                 120
```

<210> SEQ ID NO 41
<211> LENGTH: 366
<212> TYPE: DNA
<213> ORGANISM: Homo sapiens

<400> SEQUENCE: 41

| | | |
|---|---|---|
| gactagagtt ccctggcccc aggagtcata gtagggggcg ggcccgaacc agattaagag | 60 |
| tgtggtgtca catctcgcac agtaatacac ggccgtgtcc tcagattcca gtctcctcag | 120 |
| ctccatgtag gctgtgcttg tggaagtgtc cctggtcaag gtgagtctgc ccttaaactt | 180 |
| ctgtgcaaag cctgcgttac cactgttagg attcatccat cccatccact caagcccttg | 240 |
| tccagtggcc tgtcgcaccc agttgatatc ataactggtg aagatgtatc cagaagccgt | 300 |
| acaggagacc ttcactgagg ccccaggctt cttcacgtca gctgcagact gcaacagctg | 360 |
| cacctg | 366 |

<210> SEQ ID NO 42
<211> LENGTH: 378
<212> TYPE: DNA
<213> ORGANISM: Homo sapiens

<400> SEQUENCE: 42

| | |
|---|---|
| caggtgcaac tggtgcagtc tgggggaggc ttggtacagc ctggcaagtc cctgagactc | 60 |
| tcctgtgcag cctctggatt cacatttggc gattatgcca tacactgggt ccggcaagct | 120 |
| ccaggggagg gcctggagtg gtctcaggt gttacttgga gtggtactac tataggcttt | 180 |
| gcggactctg tgaagggccg attcaccatc tccagagaca acgccaagaa ttccctgtat | 240 |
| ctgtacatga acagtctgag agctgaagac acggccttgt attattgtgc cttaccatat | 300 |
| atcaactcgt ccaactacag aagagggtc gctgccttcg atatctgggg ccaagggaca | 360 |
| atggtcaccg tgtcgagt | 378 |

<210> SEQ ID NO 43
<211> LENGTH: 378
<212> TYPE: DNA
<213> ORGANISM: Homo sapiens

<400> SEQUENCE: 43

| | |
|---|---|
| actcgacacg gtgaccattg tcccttggcc ccagatatcg aaggcagcga cccctcttct | 60 |
| gtagttggac gagttgatat atggtaaggc acaataatac aaggccgtgt cttcagctct | 120 |
| cagactgttc atgtacagat acagggaatt cttggcgttg tctctggaga tggtgaatcg | 180 |

```
gcccttcaca gagtccgcaa agcctatagt agtaccactc caagtaacac ctgagaccca      240
ctccaggccc tccctggag cttgccggac ccagtgtatg gcataatcgc caaatgtgaa       300
tccagaggct gcacaggaga gtctcaggga cttgccaggc tgtaccaagc ctcccccaga      360
ctgcaccagt tgcacctg                                                    378
```

<210> SEQ ID NO 44
<211> LENGTH: 360
<212> TYPE: DNA
<213> ORGANISM: Homo sapiens

<400> SEQUENCE: 44

```
gaggtgcagc tggtggagtc tgggggaggc ttggtacagc ctggggaggtc cctgagactc     60 tcctgtgtag actctggact caccttcagt agttatggca tgcactgggt ccgcaggct      120 ccaggcgcgg ggctggagtg ggtggccgtt atttcatacg acggaaatga taaatattat    180
gcagactccg tgaagggccg attcgccatc tccagagaca atgccaagaa cacgctgtat    240
ctgcaaatga acagcctgac aatagaggac acggctgtct attattgtgc gaaagatctc    300
atagaatcaa atattgcgga ggccctctgg ggccagggaa ccctggtcac cgtgtcgagt    360
```

<210> SEQ ID NO 45
<211> LENGTH: 360
<212> TYPE: DNA
<213> ORGANISM: Homo sapiens

<400> SEQUENCE: 45

```
actcgacacg gtgaccaggg ttccctggcc ccagagggcc tccgcaatat ttgattctat     60
gagatctttc gcacaataat agacagccgt gtcctctatt gtcaggctgt tcatttgcag    120
atacagcgtg ttcttggcat tgtctctgga gatggcgaat cggcccttca cggagtctgc    180
ataatattta tcatttccgt cgtatgaaat aacggccacc cactccagcc ccgcgcctgg    240
agcctggcgg acccagtgca tgccataact actgaaggtg agtccagagt ctacacagga    300
gagtctcagg gacctcccag gctgtaccaa gcctcccca gactccacca gctgcacctc     360
```

<210> SEQ ID NO 46
<211> LENGTH: 375
<212> TYPE: DNA
<213> ORGANISM: Homo sapiens

<400> SEQUENCE: 46

```
gaggtgcagc tggtgaagtc tggggaaggc ctggtcaagc ctgggggtc cctgagactc      60 tcctgtgcag cctctggatt caccttcagg agatatgata tccactgggt ccgccagact    120
ccagggaagg gcctggagtg ggtctcatcc atcagtagtg gtggtaatta catagactac    180
gcagactctg tgaagggccg attcaccatc tccagagaca acgccaacaa tgttgtctat    240
ctacaaatga acagcctgag agccgaggac atggctgtct atttctgtgc gagagatggg    300
acgatttttg gatcggcggc gacctggcgg gcttttgata tctggggccg ggggacaatg    360
gtcaccgtgt cgagt                                                      375
```

<210> SEQ ID NO 47
<211> LENGTH: 125
<212> TYPE: PRT
<213> ORGANISM: Homo sapiens

<400> SEQUENCE: 47

Glu Val Gln Leu Val Lys Ser Gly Glu Gly Leu Val Lys Pro Gly Gly

-continued

```
              1               5                   10                  15
Ser Leu Arg Leu Ser Cys Ala Ala Ser Gly Phe Thr Phe Arg Arg Tyr
                20                  25                  30

Asp Ile His Trp Val Arg Gln Thr Pro Gly Lys Gly Leu Glu Trp Val
            35                  40                  45

Ser Ser Ile Ser Ser Gly Gly Asn Tyr Ile Asp Tyr Ala Asp Ser Val
        50                  55                  60

Lys Gly Arg Phe Thr Ile Ser Arg Asp Asn Ala Asn Asn Val Val Tyr
65                  70                  75                  80

Leu Gln Met Asn Ser Leu Arg Ala Glu Asp Met Ala Val Tyr Phe Cys
                85                  90                  95

Ala Arg Asp Gly Thr Ile Phe Gly Ser Ala Ala Thr Trp Arg Ala Phe
                100                 105                 110

Asp Ile Trp Gly Arg Gly Thr Met Val Thr Val Ser Ser
            115                 120                 125
```

<210> SEQ ID NO 48
<211> LENGTH: 375
<212> TYPE: DNA
<213> ORGANISM: Homo sapiens

<400> SEQUENCE: 48

```
actcgacacg gtgaccattg tcccccggcc ccagatatca aaagcccgcc aggtcgccgc    60
cgatccaaaa atcgtcccat ctctcgcaca gaaatagaca gccatgtcct cggctctcag   120
gctgttcatt tgtagataga caacattgtt ggcgttgtct ctggagatgg tgaatcggcc   180
cttcacagag tctgcgtagt ctatgtaatt accaccacta ctgatggatg agacccactc   240
caggcccttc cctggagtct ggcggaccca gtggatatca tatctcctga aggtgaatcc   300
agaggctgca caggagagtc tcagggaccc cccaggcttg accaggcctt ccccagactt   360
caccagctgc acctc                                                    375
```

<210> SEQ ID NO 49
<211> LENGTH: 114
<212> TYPE: PRT
<213> ORGANISM: Homo sapiens

<400> SEQUENCE: 49

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser His
                20                  25                  30

Ala Ile Ser Trp Val Arg Gln Ala Pro Gly Gln Gly Leu Glu Trp Met
            35                  40                  45

Gly Asp Ile Ile Pro Ile Leu Gly Thr Gly Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Thr Leu Thr Ser Glu Asp Thr Ala Val Tyr Tyr Cys
                85                  90                  95

Glu Leu Asp Trp Phe Tyr Ile Trp Gly Gln Gly Thr Met Val Thr Val
                100                 105                 110

Ser Ser
```

<210> SEQ ID NO 50
<211> LENGTH: 98

<212> TYPE: PRT
<213> ORGANISM: Homo sapiens

<400> SEQUENCE: 50

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys
```

<210> SEQ ID NO 51
<211> LENGTH: 122
<212> TYPE: PRT
<213> ORGANISM: Homo sapiens

<400> SEQUENCE: 51

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Asn Phe
            20                  25                  30

Ala Met Ser Trp Val Arg Gln Ala Pro Gly Lys Gly Leu Glu Trp Val
        35                  40                  45

Ala Ala Ile Gly Gly Arg Ser Gly Thr Thr Phe Tyr Ala Asp Ser Val
    50                  55                  60

Lys Gly Arg Phe Thr Ile Ser Arg Asp Asn Ser Lys Asn Thr Val Tyr
65                  70                  75                  80

Leu Glu Met Asn Ser Leu Arg Ala Glu Asp Thr Ala Ile Tyr Tyr Cys
                85                  90                  95

Ala Lys Arg Gly Arg Gly Gly Tyr Lys Tyr Tyr Gly Met Asp Val Trp
            100                 105                 110

Gly Gln Gly Thr Thr Val Thr Val Ser Ser
        115                 120
```

<210> SEQ ID NO 52
<211> LENGTH: 342
<212> TYPE: DNA
<213> ORGANISM: Homo sapiens

<400> SEQUENCE: 52

```
caggtgcagc tggtgcagtc tggggctgag gtgaagaagc ctgggtcctc ggtgaaggtc      60
tcctgcaagg cttctggagg caccttcagc agtcatgcta tcagctgggt gcgacaggcc     120
cctggacaag ggcttgagtg gatgggagac atcatcccta tccttggtac aggaaactac     180
gcacagaagt tccagggcag agtcacgatt accgcggacg agtccacgag cacagcctac     240
atggagctga gcaccctgac atctgaggac acggccgtgt attactgtga acttgactgg     300
ttctatatct ggggccaagg gacaatggtc accgtgtcga gt                        342
```

<210> SEQ ID NO 53

-continued

```
<211> LENGTH: 342
<212> TYPE: DNA
<213> ORGANISM: Homo sapiens

<400> SEQUENCE: 53
actcgacacg gtgaccattg tcccttggcc ccagatatag aaccagtcaa gttcacagta      60
atacacggcc gtgtcctcag atgtcagggt gctcagctcc atgtaggctg tgctcgtgga     120
ctcgtccgcg gtaatcgtga ctctgccctg gaacttctgt gcgtagtttc ctgtaccaag     180
gatagggatg atgtctccca tccactcaag cccttgtcca ggggcctgtc gcacccagct     240
gatagcatga ctgctgaagg tgcctccaga agccttgcag agaccttca ccgaggaccc      300 aggcttcttc acctcagccc cagactgcac cagctgcacc tg                        342

<210> SEQ ID NO 54
<211> LENGTH: 366
<212> TYPE: DNA
<213> ORGANISM: Homo sapiens

<400> SEQUENCE: 54
gaggtgcagc tggtggagtc tgggggagac ttggtacagc ctggggggtc cctgagactc      60
tcctgtgcag cctctggatt cacctttagc aactttgcca tgagctgggt ccgccaggct     120
cccgggaagg ggctggagtg gtcgcggct attggcggta gaagtggtac cacattctac      180
gcggactccg tgaagggccg gttcaccatc tccagagaca attccaagaa cacggtctat      240
ctggaaatga acagtctgag agccgaggac acagccattt attactgtgc gaaaagaggg     300 cgcgggggt ataagtatta tgggatggac gtctgggcc aggggaccac ggtcaccgtg       360
tcgagt                                                                 366

<210> SEQ ID NO 55
<211> LENGTH: 366
<212> TYPE: DNA
<213> ORGANISM: Homo sapiens

<400> SEQUENCE: 55
actcgacacg gtgaccgtgg tcccctggcc ccagacgtcc atcccataat acttataccc      60
cccgcgccct cttttcgcac agtaataaat ggctgtgtcc tcggctctca gactgttcat     120
ttccagatag accgtgttct tggaattgtc tctggagatg gtgaaccggc ccttcacgga     180
gtccgcgtag aatgtggtac cacttctacc gccaatagcc gcgacccact ccagccccttt    240 cccgggagcc tggcggaccc agctcatggc aaagttgcta aaggtgaatc cagaggctgc     300
acaggagagt ctcagggacc ccccaggctg taccaagtct ccccagact ccaccagctg      360 cacctc                                                                 366
```

METHOD FOR DIAGNOSIS AND TREATMENT OF HAEMOPHILIA A PATIENTS WITH AN INHIBITOR

FIELD OF THE INVENTION

This invention is in the fields of diagnosis and medical treatment. More particularly, the invention provides means and methods for diagnosing the presence of inhibitory antibodies directed against factor VIII in the blood of human individuals, and provides means, pharmaceutical compositions and methods for treating human individuals in which such inhibitory antibodies occur.

BACKGROUND OF THE INVENTION

Haemophilia A is an X-linked bleeding disorder which is characterized by the functional absence of blood coagulation factor VIII. Depending on the residual factor VIII activity in the plasma of the patient, haemophilia A can be classified as severe (factor VIII<1%), moderate (factor VIII 1-5%) or mild (>5%). Bleeding episodes in patients with haemophilia A can be effectively controlled by intravenous administration of purified factor VIII concentrates. These factor VIII-concentrates may be derived from pools of human plasma. Alternatively, recombinant factor VIII produced by genetically engineered eukaryotic cells may be used as a starting material for the preparation of factor VIII concentrates.

A serious complication of current haemophilia A treatment constitutes the development of neutralizing antibodies directed against factor VIII. These antibodies, commonly termed factor VIII inhibitors, arise in approximately 25% of the patients with severe haemophilia A, usually after 5-20 exposure-days (Ehrenforth et al. 1992, Lancet 339: 594-598). In patients with moderate and mild haemophilia A, anti-factor VIII antibodies occur less frequently and this is most likely due to induction of tolerance by endogenous factor VIII present in the plasma of this group of patients (McMillan et al. 1988, Blood 71: 344-348). Antibodies to factor VIII may develop with low frequency in healthy individuals.

Diagnosis of factor VIII inhibitors is commonly performed using the so-called Bethesda assay (Kasper et al. 1975, Thromb. Diath. Haemorrh. 34: 869-872). In this assay equal amounts of normal plasma and dilutions of inhibitor plasma are incubated for two hours at 37° C. Next, residual factor VIII activity is determined and compared to control incubation in which normal plasma is incubated with 0.1 M imidazole for 2 hours at 37° C. The amount of inhibitor is expressed in Bethesda units; one Bethesda unit corresponds to the amount of inhibitor that is capable of reducing the activity of factor VIII in normal plasma by 50%. A recent study has proposed several adaptations to the original assay system which serve to improve the stability of factor VIII during the assay (Verbruggen et al. 1995, Thromb. Haemostas. 73: 247-251). This so-called "Nijmegen modification" of the Bethesda assay is particularly useful for the detection of low titre factor VIII inhibitors. It should be noted that the Bethesda assay does not provide information on the epitopes of factor VIII inhibitory antibodies.

The occurrence of factor VIII-inhibiting antibodies renders factor VIII replacement therapy inadequate. Several treatment options are available to the clinician. Low titre inhibitors (up to 5-10 BU/ml) are usually treated with infusion of high doses of factor VIII. A subset of factor VIII inhibitors does not cross react with porcine factor VIII. Porcine factor VIII has been used for management of patients with an inhibitor. Administration of porcine factor VIII may present with side effects. After multiple treatment 30-50% of the patients develop antibodies that neutralize the activity of the administered porcine factor VIII.

An alternative treatment of patients with factor VIII inhibitor constitutes the use of factor VIII bypassing agents. Activated prothrombin concentrate complexes (APCC) have been used to bypass the activity of factor VIII. APCC has been used successfully to control bleeding episodes in a large number of patients with an inhibitor. However, treatment is not effective in all cases and an anamnestic rise in the titre of the inhibitor following administration of APCC (most likely due to trace amounts of factor VIII in the preparation) has been reported in a number of patients. In the last 5 years recombinant factor VIIa has become available as a new factor VIII bypassing agent for the treatment of patients with an inhibitor (Lusher et al. 1996. Haemostasis 26 (suppl. 1): 124-130). Recombinant factor VIIa has been successfully used to control the bleeding episodes in patients with an inhibitor. Treatment by this agent is however limited by the short half-life of this compound in the circulation which requires multiple infusions at relatively short time intervals. APC-resistant factor V has recently been suggested as an alternative means to bypass the biological activity of factor VIII inhibitors (WO 95/29259). The agents described above do not act directly on factor VIII inhibitors but merely serve to bypass factor VIII by infusion of large amounts of clotting factor concentrates with increased procoagulant activity.

Other methods of inhibitor neutralization have been proposed but their effectiveness has not been convincingly shown. Immunoglobulin preparations derived from plasma of healthy donors has been proposed as an active suppressor of factor VIII inhibitors (Sultan et al. 1984, Lancet 333, 765–768). Despite success in patients with acquired haemophilia A and high titre inhibitors, immunoglobulin preparations are not applied universally for treatment of patients with an inhibitor. The beneficial effects of immunoglobulin preparations in these patients have been attributed to the presence of anti-idiotypic antibodies that neutralize the activity of factor VIII inhibitors. Indeed in some patients the decline in the level of factor VIII inhibitors coincided with the appearance of anti-idiotypic antibodies (Sultan et al. 1987, Proc. Natl. Acad. Sci. USA 84: 828-831). Control of factor VIII inhibitors by anti-idiotypic antibodies in both haemophilia A patients and healthy individuals has been strongly advocated by some investigators (Gilles et al. 1996, J. Clin. Inv. 97: 1382-1388). The same group has proposed that infusion of antigen-antibody complexes in patients with inhibitors may accelerate a decline in anti-factor VIII antibodies in patients with an inhibitor (U.S. Pat. No. 5, 543, 145). It has been proposed that this decline is mediated by an increase in the number of anti-idiotypic antibodies which are induced by the infused antigen-antibody complexes. The factor VIII specific antibody used in this treatment protocol is derived from plasma of patients with an inhibitor. Obviously, this presents a heterogeneous mixture of antibodies and no details with respect to the epitope specificity of these antibodies are available. Also the primary structure of the antibodies in these antigen-antibody preparations has not been disclosed.

SUMMARY OF THE INVENTION

This invention relates to methods for diagnosis and treatment using inhibitory antibodies directed against factor VIII. Methods are disclosed that show how to arrive at nucleotide and amino acid sequences that encode factor VIII specific antibodies. This invention discloses diagnostic tests that allow for detection of nucleotide and amino acid sequences that encode factor VIII specific antibodies within a heterogeneous mixture of antibody-encoding nucleotide or amino acid sequences. This invention further discloses how to use recombinant antibody fragments which bind specifically to factor VIII as novel therapeutic agents for the treatment of patients with factor VIII inhibitors.

The invention provides a polynucleotide in substantially isolated form, comprising a contiguous nucleotide sequence (a) coding for a human antibody with factor VIII specificity, or (b) complementary to a nucleotide sequence coding for a human antibody with factor VIII specificity, or (c) capable of selectively hybridizing under stringent conditions to nucleotide sequence (a) or (b).

Preferably, the contiguous nucleotide sequence is at least 8, preferably at least 10 nucleotides.

In a preferred embodiment, the invention provides a probe or primer which comprises a polynucleotide as defined herein, optionally further comprising a detectable label, such as a radioactive atom or group, an enzyme, a fluorescent or luminescent group, a dye or biotin.

The invention also provides an assay kit for detecting nucleic acid coding for a human antibody with factor VIII specificity, comprising a probe or primer as defined herein in a suitable container.

Furthermore, the invention provides a nucleic acid amplification and detection kit for detecting nucleic acid coding for a human antibody with factor VIII specificity, comprising a pair of primers as defined herein capable of priming the synthesis of cDNA, and optionally further comprising a probe as defined herein capable of selectively hybridizing to (the complement of) a region of the nucleic acid to be detected between and not including the sequences from which the primers are derived.

The invention provides a method for assaying a sample for the presence or absence of nucleic acid coding for a human antibody with factor VIII specificity, comprising contacting the sample with a probe as defined herein under conditions that allow the selective hybridization of said probe to the (complement of the) nucleic acid to be detected in the sample, and determined whether polynucleotide duplexes comprising said probe are formed.

The invention also provides a method for assaying a sample for the presence or absence of nucleic acid coding for a human antibody with factor VIII specificity, comprising subjecting nucleic acid present in the sample to a nucleic acid amplification process using a pair of primers as defined herein capable of priming the synthesis of cDNA, contacting the nucleic acid resulting from the amplification process with a probe as defined herein under conditions that allow the selective hybridization of said probe to the (complement of the) nucleic acid to be detected in the sample, and determining whether polynucleotide duplexes comprising said probe are formed.

Furthermore, the invention provides a method of producing a recombinant polypeptide, comprising providing a polynucleotide coding for said polypeptide, preparing a recombinant vector containing said polynucleotide operably linked to a control sequence capable of providing for the expression of the polynucleotide by a host cell, transforming a host cell with said recombinant vector, growing said host cell under conditions that provide for the expression of the polynucleotide and optionally isolating the thus produced polypeptide, wherein said polynucleotide codes for a human antibody with factor VIII specificity, or a fragment or derivative thereof capable of specific binding to factor VIII.

According to another aspect, the invention provides a polypeptide in substantially isolated form, comprising a contiguous amino acid sequence corresponding to or mimicking a fragment or derivative of a human antibody with factor VIII specificity capable of specific binding to factor VIII. In a preferred embodiment of the invention, the contiguous amino acid sequence is capable of reducing the activity of factor VIII inhibiting antibodies.

Preferably, the fragment is (part of) a variable region of the heavy chain or light chain of said antibody, and the derivative is preferably a single chain Fv fragment of said antibody.

The invention furthermore provides an antibody in substantially isolated form, comprising a recombinant human antibody with factor VIII specificity.

The invention furthermore provides a pharmaceutical composition for the treatment of factor VIII inhibition in a human individual, comprising a polypeptide as defined herein or an antibody as defined herein, together with a pharmaceutically acceptable carrier. Optionally, the composition further contains factor VIII, or a substitute of factor VIII.

The invention also provides a method of treatment of factor VIII inhibition in a human individual comprising administering (an effective amount to reduce or prevent said factor VIII inhibition of) a polypeptide as defined herein or an antibody as defined herein, optionally together with factor VIII or a substitute of factor VIII.

BRIEF DESCRIPTION OF THE DRAWINGS

FIG. 3 shows the nucleotide sequence of clone EL14 (SEQ. ID. NO: 19) and clone IT2 (SEQ. ID. NO: 21). The nucleotide sequence of both clones is aligned with the nucleotide sequence of the germline sequences DP-10 (SEQ. ID. NO: 20) (for EL14) and DP-14 (SEQ. ID. NO: 22) (for IT2). The different regions of the variable part of the heavy chain are indicated in the following order: framework 1, CDR1, framework 2, CDR2, framework 3, CDR3 and framework 4. Homology of clones EL14 and IT2 with the germline sequences DP-10 and DP-14 is indicated by horizontal bars (–). Differences are indicated by the nucleotides that occur in the germline sequences DP-10 and DP-14. Note that both CDR3 and framework 4 are not derived from the germline sequences DP-10 and DP-14. Consequently, no homology is given for this part of the nucleotide sequence.

FIG. 4A gives the amino acid sequence (VHEL-14 (SEQ. ID. NO. 23) and VHIT-2 (SEQ. ID. NO: 25)) derived of the nucleotide sequence of clone EL14 (SEQ. ID NO: 19) and IT2 (SEQ. ID. NO: 21). Deviations in the amino acid sequence of the germline segments DP-10 (SEQ. ID. NO: 24) and DP-14 (SEQ. ID. NO: 26) are indicated in the lower lines. Framework is abbreviated as "FR".

FIG. 4B compares the amino acid sequence of three related clones that are derived from the germline segment DP-14 (SEQ. ID. NO: 26). The amino acid sequences of clone IT2 (SEQ. ID. NO: 25), clone EL5 (SEQ. ID. NO: 27) and clone EL25 (SEQ. ID. NO: 28) are compared to that of the germline segment DP-14 (SEQ. ID. NO: 26). Deviations in amino acid sequence are indicated for each clone. Note that some amino acid substitutions are shared by the three different clones.

FIG. 4C compares the amino acid sequences of the third variable loop (CDR3) of the heavy chain of clone EL14 (SEQ. ID. NO: 29) and IT2 (SEQ. ID. NO: 30). Homologous amino acid residues are indicated by vertical lines. Dots denote amino acids related in charge or hydrophobicity.

FIG. 7A shows the neutralization of the inhibitory activity of the murine monoclonal antibody CLB-CAg 117 by scFv-EL14. Antibody CLB-CAg 117 was diluted till a value of 2 Bu/ml which corresponds with a residual factor VIII activity of about 25%. Increasing amounts of scFv-EL14 were capable of neutralizing the inhibitory activity of CLB-CAg 117 (closed circles). A concentration of 0.75 μg/ml suffices to restore factor VIII activity to its original level. ScFv-EL14 did not affect the inhibitory activity of the murine monoclonal antibody CLB-CAg A (open circles). On the y-axis residual factor VIII activity is depicted. On the x-axis the amount of scFc added is given in μg/ml.

FIG. 7B shows the neutralization of the inhibitory activity of CLB-CAg 117 by scFv-IT2 (closed circles). A concentration of 65 μg/ml is needed to restore factor VIII activity to its original level. ScFv-IT2 did not affect the inhibitory activity of CLB-CAg A (open bars). On the y-axis residual factor VIII activity is depicted. On the x-axis the amount of scFv added is given in μg/ml.

FIG. 9A shows the deduced amino acid sequence of recombinant antibody fragments specific for the A3-C1 domain. The amino acid sequence of germline variable heavy chain gene segments DP-15 (SEQ. ID. NO: 31), DP31 (SEQ. ID. NO: 33), DP49 (SEQ. ID. NO: 35) and DP77 (SEQ. ID. NO: 37) is given. Deviations in amino acid sequence from these germline gene segments are indicated for clone B38 (SEQ. ID. NO: 32), B18 (SEQ. ID. NO: 34), B35 (SEQ. ID. NO: 36) and B04 (SEQ. ID. NO: 38). Also the amino acid of the CDR3 and FR4 of the A3-C1 specific recombinant antibodies encoded by clone B38, B18, B35 and B04 is given.

FIG. 9B gives the nucleotide (SEQ. ID. NO: 39), complementary strand (SEQ. ID. NO: 41), and amino acid (SEQ. ID. NO: 40) sequence of the variable heavy chain domain of clone B38.

FIG. 9C gives the nucleotide (SEQ. ID. NO: 42), complementary strand (SEQ. ID. NO: 43), and amino acid (SEQ. ID. NO: 34) sequence of the variable heavy chain domain of clone B18.

FIG. 9D gives the nucleotide (SEQ. ID. NO: 44), complementary strand (SEQ. ID. NO: 45), and amino acid (SEQ. ID. NO: 36) sequence of the variable heavy chain domain of clone B35.

FIG. 9E gives the nucleotide (SEQ. ID. NO: 46), complementary strand (SEQ. ID. NO: 48), and amino acid (SEQ. ID. NO: 47) sequence of the variable heavy chain domain of clone B04.

FIG. 11A shows the deduced amino acid sequence (SEQ. ID. NOS: 49 and 51) of recombinant antibody fragments specific for the factor VIII heavy chain. The amino acid sequence of germ line variable heavy chain gene segments DP10 (SEQ. ID. NO: 24) and DP47 (SEQ. ID. NO: 50) is given. Deviations in amino acid sequence from these germline gene segments are indicated for two clones that encode recombinant antibodies that bind to the factor VIII heavy chain. Also the amino acid of the CDR3 and FR4 of the factor VIII heavy chain specific recombinant antibodies encoded by the two clones is given.

FIGS. 11B and C give the nucleotide (SEQ. ID. NOS: 52 and 54), complementary strand (SEQ. ID. NOS: 53 and 55) and amino acid (SEQ. ID. NOS: 49 and 51) sequence of the variable heavy chain domain of two clones that encode recombinant antibodies that bind specifically to the factor VIII heavy chain.

DETAILED DESCRIPTION OF THE INVENTION

Figure 1:
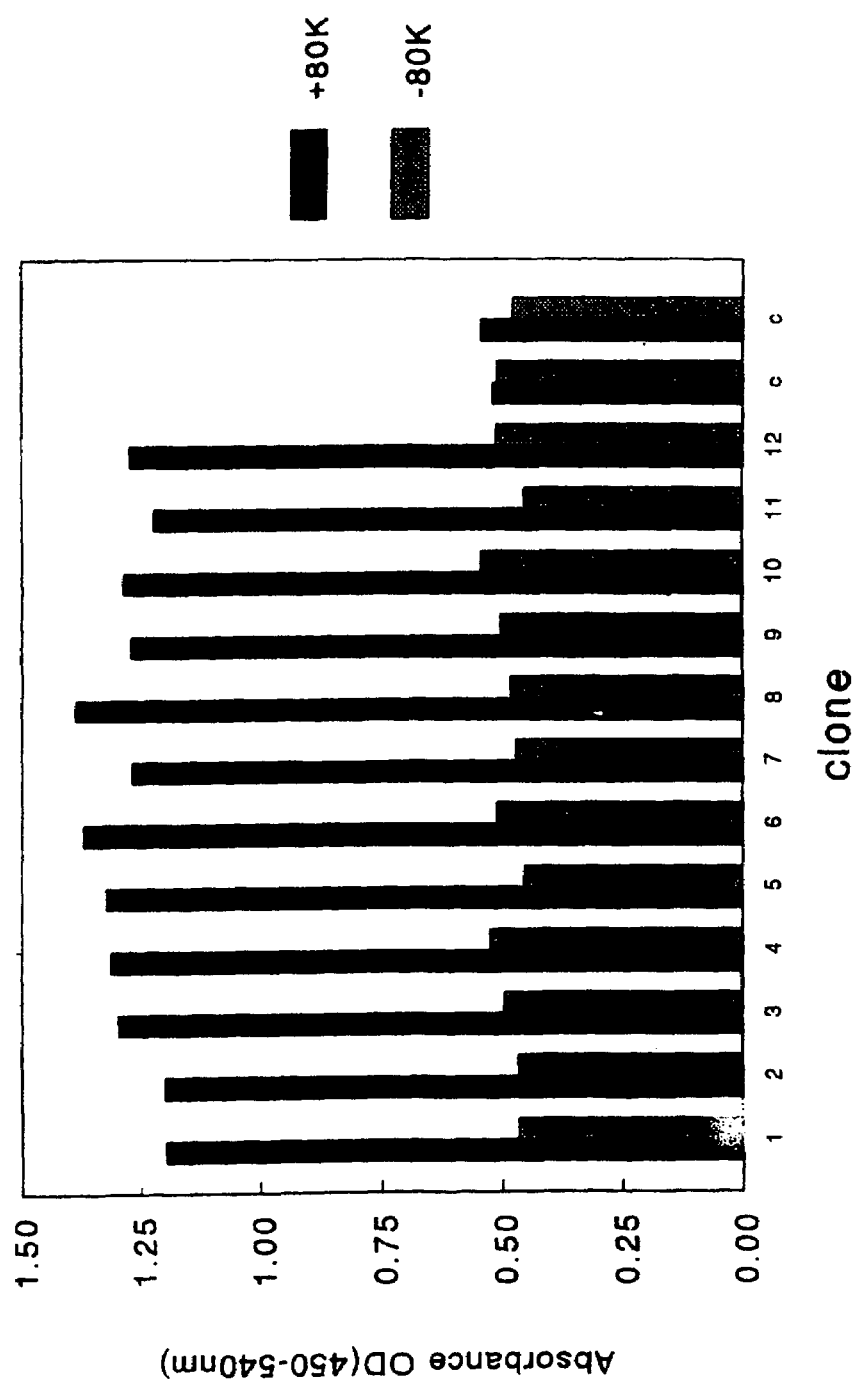
FIG. 1 shows the light chain specificity of 12 clones obtained after 4 rounds of panning of the IgG4-specific library described in Example 2. Phage expressing recombinant antibodies were incubated on microtiter wells which contained factor VIII light chain (black bars; '80K). To correct for background binding phage were also incubated on microtiter wells that did not contain factor VIII light chain (grey bars; +80K). On the Y-axis the OD(450-540 nm) is depicted. Two clones (c) express antibody fragments that do not bind specifically to the factor VIII light chain.

A number of investigators have addressed the epitope-specificity and mode of action of factor VIII inhibitory antibodies. Molecular cloning of the factor VIII cDNA revealed that factor VIII consists of a series of repeated domains which appear in the order A1-A2-B-A3-C1-C2. In plasma, factor VIII circulates as a heterodimer which consists of a heavy chain of variable length (90-220 kDa) and a light chain of 80 kDa. The factor VIII light chain consists of the domains A3-C1-C2 while the factor VIII heavy chain comprises the domains A1-A2-B. Heterogeneity of the factor VIII heavy chain is caused by limited proteolysis within the B-domain which contains several sites that are sensitive towards proteolytic cleavage. In plasma, factor VIII circulates in complex with von Willebrand factor, a large multimeric protein involved in the initial steps of platelet adhesion to a damaged vessel wall. Binding to von Willebrand factor protects factor VIII from proteolytic degradation. The physiological importance of this interaction is underscored by the low levels of factor VIII in plasma of patients that lack von Willebrand factor. Factor VIII is a precursor molecule which upon activation functions as a cofactor for factor IXa in the phospholipid and $Ca^{2+}$-dependent conversion of factor X to factor Xa. Activation of factor VIII involves proteolytic cleavages in both the heavy and light chain of factor VIII. Thrombin is considered to be the physiological activator of factor VIII and cleaves at $Arg^{372}$, $Arg^{740}$ and $Arg^{1689}$ of factor VIII. Thrombin activated factor VIII thus consists of a hetero-trimer of the separate A1 and A2-domains and the cleaved factor VIII light chain (A3-C1-C2). Cleavage at $Arg^{1689}$ of the factor VIII light chain results in removal of amino-acid sequence $Glu^{1649}$-$Arg^{1689}$ which is essential for binding of factor VIII to von Willebrand factor. Sofar, three major binding sites for factor VIII inhibitors have been characterized (Scandella et al. 1994, Blood 86: 1811-1819; Healey et al. 1995, J. Biol. Chem. 270: 14505-14509; Fijnvandraat et al. 1998, Blood 91: 2347-2352).

Amino acid residues $Val^{2248}$-$Ser^{2312}$ in the C2-domain constitute a binding site for factor VIII inhibitors. The large size of this epitope suggests that a number of antibodies which bind to different amino acid regions in this area occur in plasma of patients with inhibitors of C2-specificity. The mechanisms of action of anti-C2 antibodies has been explored in considerable detail. Most of these antibodies interfere with binding of factor VIII to phospholipids. Furthermore, some of the antibodies with C2-specificity also inhibit the interaction of factor VIII with its carrier von Willebrand factor. A new mechanism for inhibition of factor VIII by a human alloantibody has been described recently (Saenko et al. 1996, J. Biol. Chem. 271: 27424-27431). A human alloantibody that binds only to the amino-terminal portion ($Val^{2248}$-$Gly^{2285}$) of the C2-epitope has been shown to inhibit the thrombin induced release of factor VIII from von Willebrand factor.

Amino acid residues $Arg^{484}$-$Ile^{508}$ in the A2-domain of factor VIII constitute a major epitope for factor VIII inhibitors. Studies on the mechanism of inhibition of anti-A2 antibodies have shown that anti-A2 antibodies interfere with conversion of factor X to Xa by the lipid bound factor VIIIa-factor IXa-complex (Lollar et al., 1995). The anti-A2-antibodies do not interfere with binding of factor X to the factor VIIIa-factor IXa complex but simply limit the conversion of factor X.

A third major epitope of factor VIII inhibitors has been found in the A3-domain of factor VIII. Binding of inhibitory antibodies was dependent on the presence of amino acids $Gln^{1178}$-$Met^{1823}$. Previous studies have shown that this site constitute a binding site for factor IXa and indeed antibodies binding to this site interfered with complex assembly of factor VIIIa and factor IXa (Fijnvandraat et al. 1998. Blood 91: 2347-2352). In a number of patients with an inhibitor, inhibitory antibodies directed against other epitopes have been observed. An early study has shown that inhibitory antibodies may recognize amino acid region $Met^{336}$-$Arg^{372}$ of factor VIII (Ware et al. 1998. Proc. Natl. Acad. Sci USA 85: 3165-3169). The mechanism of inhibition has not yet been explored but recently a binding site for factor X has been proposed in this part of the factor VIII molecule (Lapan, K. A. and Fay, P. J. 1997. J. Biol. Chem. 272: 2082-2088).

The restricted epitope specificity of factor VIII inhibitors suggests that a limited number of dominant B-cell epitopes is involved in the immune response to factor VIII. Apparently, human anti-factor VIII antibodies synthesized by B-cell clones from a variety of patients are surprisingly similar with respect to epitope specificity. This suggests that the primary amino acid and nucleotide sequence of antibodies with factor VIII specificity is similar at the molecular level. Based on this it is desirable to define the presence and epitope specificity of anti-factor VIII antibodies by simply addressing the presence of nucleotide sequences that correspond to antibodies with factor VIII inhibiting capacity. Sofar, the primary sequences of anti-factor VIII antibodies have been poorly defined. Davies and co-workers have suggested an association between factor VIII inhibitors and use of VH gene segment DP73 (Davies et al. 1997. Thromb. Haemostas. supplement: 2352A). The nucleotide and primary amino acid sequence of these antibodies has not been disclosed and details with respect to the epitope specificity of these antibodies are lacking. Clearly, there is a need to define the primary amino acid and nucleotide sequence of factor VIII antibodies in more detail. Such sequence information can be used to design diagnostic tests which can be used to monitor the occurrence of B-cell clones that produce factor VIII inhibitors in patients with haemophilia A. These diagnostic tests can be extremely sensitive and give information on the epitope specificity of factor VIII inhibitors.

Studies directed at defining the epitope specificity and mode of action of these antibodies are limited by the heterogeneity of these antibodies in the plasma of these patients. Clearly, more stringent diagnostic criteria would be required to define the properties of factor VIII inhibitors in more detail.

A sudden increase in the frequency of inhibitor development in a group of previously treated patients has been associated with a particular pasteurized factor VIII concentrate manufactured in the Netherlands (Roosendaal et al. 1993. Blood 81: 2180-2186). These factor VIII inhibitors are directed against the factor VIII light chain and epitope mapping revealed that the majority of inhibitors reacted with epitopes in the A3-C1 and the C2-domain of factor VIII (Sawamoto et al. 1998. Thromb. Haemostas. 79: 62-68). Recently, a second pasteurized factor VIII concentrate has been implicated in the development of inhibitors in a group of previously treated patients. Also in this case the inhibitory antibodies were predominantly of factor VIII light chain specificity (Peerlinck et al. 1997. Thromb. Haemostas. 77: 80-86). It has been suggested that inhibitor development in these patients is due to small alterations in the factor VIII molecule which have been induced by the manufacturing process. This may indicate that the antibodies that developed in these patients have different properties compared to the factor VIII inhibitory antibodies that develop in other patients. Clearly, knowledge of nucleotide and amino acid sequence of factor VIII specific antibodies could provide additional information on the etiology of factor VIII inhibitor which is desirable for the characterization of the antibody response in patients who have received these factor VIII concentrates.

Until now, the primary nucleotide and amino acid sequence of anti-factor VIII antibodies has not been disclosed. This invention describes the nucleotide sequences that encode human antibodies with factor VIII-specificity. Based on the primary sequence of these antibodies, oligonucleotide primers are designed that allow for detection of B-cells that produce antibodies with affinity for factor VIII. Detection of factor VIII specific B-cells may be accomplished using both mRNA, cDNA or DNA which are derived from lymphocytes of patients. Genomic DNA, RNA and cDNA are prepared from lymphocytes by methods that are generally known in the art. Some methods for the detection of factor VIII specific B-cell clones are listed below. Other methods for the detection of nucleotide sequences of factor VIII specific antibodies, disclosed in this invention, are considered to fall within the scope of this invention. Selective amplification of heavy chain variable sequences (VH-genes) can be used to detect nucleotide sequences that encode antibodies that are part of the human antibody repertoire that can bind specifically to factor VIII. The variable part of the human heavy chain is assembled from the variable heavy chain regions (VH), the diversity regions (D) and the joining regions (J). Fusion of these three different gene segments is not a precise event and this so-called "junctional diversity", together with the process of nucleotide addition and deletion, results in the generation of the hypervariable complementary determining region 3 CDR3. The human light chain is assembled in a similar manner but lacks diversity region D. Additional sequence diversity of both heavy and light chain sequences is generated by somatic hypermutation and together with the mechanisms outlined above this ultimately results in the generation of high affinity antibodies. Knowledge on the nucleotide sequences that encode factor VIII-specific antibody allows for the detection of this specific antibody in the repertoire of patients who are at risk of developing factor VIII-specific antibodies (such as haemophilia A patients who are treated with factor VIII or patients with acquired haemophilia). Amplification may be performed with a combination of oligonucleotide primers directed against constant regions or variable regions of heavy and light chain of factor VIII-specific antibodies. Detection of factor VIII specific antibodies may be performed using one oligonucleotide primer derived from the variable parts of the nucleotide sequences encoding factor VIII antibodies and one oligonucleotide primer that is derived from the constant regions of factor VIII specific antibodies. Detection may also be performed using two oligonucleotide primers specific for variable parts of the nucleotide sequence that encodes an antibody that binds to factor VIII. The methods described herein also include the amplification of immunoglobulin genes using oligonucleotide primers that are directed against the constant regions of the immunoglobulin genes. Subsequent detection of nucleotide sequences of factor VIII specific antibodies can be performed using selective hybridization with (radiolabelled) oligonucleotide primers that are directed against the variable parts of the nucleotide sequence encoding factor VIII specific antibodies. From the above it follows that oligonucleotide primers are preferentially but not exclusively directed towards the constant and variable regions of factor VIII specific antibodies. In example 5, methods are disclosed that can be used to detect the presence of factor VIII specific antibodies in a mixture of nucleotide sequences. Combination of oligonucleotide primers derived from the nucleotide sequence of factor VIII specific antibodies can be used to directly assess the presence of factor VIII specific antibodies in the antibody-repertoire of patients. Alternatively, analysis by methods that include but are not limited to sequencing analysis, re-amplification of obtained fragments with more specific oligonucleotide primers, digestion with restriction enzymes and selective hybridization may be utilized to address the presence of factor VIII antibodies. Quantification of the amount of nucleotide sequences encoding factor VIII antibodies may be obtained by various methods that are generally known in the art and include but are not limited to the following. The amount of radioactivity incorporated into a PCR-fragment that encodes part of a factor VIII specific antibody can be determined. Furthermore, radioactively labelled oligonucleotide probes can be used to estimate the amount of a nucleotide sequence encoding a factor VIII specific antibody in a mixture of DNA fragments that code for part of a patients antibody repertoire. Quantitative PCR-amplification can be performed using for example dye-modified oligonucleotide primers which allow for direct monitoring of the amount of PCR-product generated during amplification.

Other methods that selectively detect and quantify specific nucleotide sequences that encode factor VIII specific antibodies may be devised by an average expert in the art. These methods are considered to fall within the scope of the present invention.

Examples 1-10 provide details on the identification and detection of nucleotide sequences that encode factor VIII specific antibodies in haemophilia patients. These examples teach how to arrive at the nucleotide sequence of factor VIII inhibitors and provide information on how to use this information for the detection of factor VIII specific antibodies.

This invention discloses the nucleotide and primary amino acid sequences of factor VIII specific antibodies.

Factor VIII inhibitors are commonly directed against three major epitopes on factor VIII within the A2-A3 and C2-domain of factor VIII. In Example 4 the nucleotide and amino acid sequence of anti-C2 antibodies is disclosed. In examples 8 and 9, the nucleotide and amino acid sequence of anti-A2 and anti-A3-C1 antibodies is disclosed. This invention teaches how to arrive at the nucleotide and amino acid sequence of factor VIII specific antibodies and the methods disclosed in this invention can be used to derive the nucleotide and amino acid sequence of anti-factor VIII antibodies with specificity for other domains of factor VIII which are a target for factor VIII inhibitors. Anti-factor VIII antibodies encoded by the nucleotide sequences disclosed here, can be used for the development of therapeutic agents that are capable of limiting the biological activity of factor VIII inhibitors. These therapeutic agents preferentially contain, but are not limited to:

1. The antibody fragments (or agents based on the nucleotide or amino acid sequence) can be used for the generation of anti-idiotypic antibodies. Antibody fragments can be either administered together with factor VIII or administered alone. Also, peptides or related agents which are based on the primary amino acid sequence of the variable parts of factor VIII specific antibodies can be used to induce the formation of anti-idiotypic antibodies direct against factor VIII inhibitors. Anti-idiotypic antibodies can also be obtained by screening large (semi-synthetic) libraries that encode a wide variety of recombinant antibodies. The preparation of anti-idiotypic antibodies can also take place in animals that include but are not limited to mouse by injection of recombinant antibody disclosed in this invention. Anti-idiotypic antibodies can subsequently be obtained by methods that are known to those skilled in the art. An anti-idiotypic response to factor VIII specific antibodies may also be obtained by injection of DNA encoding part of the nucleotide sequences of factor VIII specific antibodies which can be obtained by the methods outlined in this invention. Immunization by injection of DNA is considered to be only modestly immunogenic and other agents are needed to obtain a sufficiently high immune response. Co-injection of plasmid DNA encoding IL-2, GM-CSF and tetanus toxoid has been used to enhance the immune response to injected DNA (Spellerberg et al. 1997. J. Immunol. 15:1885-1892). Similar methods can be applied to enhance the immune response towards DNA fragments encoding factor VIII specific antibodies.
2. The recombinant antibody fragments described in this invention can be used as a therapeutic for treatment of patients with an inhibitor. Examples 7 and 10 disclose that recombinant antibody fragments (termed scFv's) which bind specifically to the C2-domain, interfere with binding of inhibitory antibodies to factor VIII. These scFv's can be used for treatment of patients with inhibitory antibodies directed against the C2-domain. This invention discloses how to arrive at recombinant antibody fragments that bind specifically to the A2, A3-C1 and C2-domain of factor VIII. Using the methods outlined in this invention additional antibody fragments directed against these and other regions on factor VIII may be obtained. These regions include but are not limited to $Arg^{484}$-$Ile^{508}$ in the A2-domain, $Gln^{1778}$-$Met^{1823}$ in the A3-domain and $Val^{2248}$-$Ser^{2312}$ in the C2-domain. Recombinant antibodies directed against multiple epitopes preferentially will be part of a pharmaceutical preparation since most patients have inhibitory antibodies directed against multiple epitopes on factor VIII. The inhibitor neutralizing activity of the recombinant antibody fragments described in this invention may be modified by the introduction of point mutations in the constant and variable parts of these fragments. Furthermore, the recombinant antibody fragments described in this invention may be cloned into vectors which allow for expression of these fragments for example as Fab-fragment. Other vectors for expression of antibodies and antibody fragments are available to an average expert in the field (see for example: "Antibody Engineering; A Practical Approach" edited by Mc Cafferty et al. 1996. Oxford University Press). Methods to increase the affinity of recombinant antibodies or antibody fragments are readily available and can be used to modulate the biological activities of the recombinant antibody fragments described in this invention. Peptides and peptide-related agents which have been designed based on the amino acid sequence of the recombinant antibodies described in this invention (for example peptides derived from the amino acid sequence of CDR3) can be used to interfere with the activity of factor VIII inhibitors.

In summary, this invention provides an improved method to define factor VIII inhibitory antibodies. The methods described result in definition of the nucleotide sequence of factor VIII inhibitors and teaches how to utilize this information for the development of improved methods for the detection of factor VIII inhibitors. This invention also discloses pharmaceutical preparations, derived from the nucleotide and/or primary amino acid sequence of factor VIII specific antibodies, that can be used in the treatment of haemophilia A patients with inhibitory antibodies directed against factor VIII. The dose of the therapeutic agents to be administered to a patient, obviously depends on the affinity of the therapeutic agent for factor VIII. The affinity of the recombinant antibody fragments described in this invention can vary considerably as is disclosed in Examples 6 and 7. The dose to be administered also depends on bodyweight of the patient, the titre of the factor VIII inhibitor and the biological activities of the different components of the therapeutic agent used. The dose to be administered can be estimated according to methods that are disclosed in Examples 7 and 10. These methods may be complemented with dose finding studies which involve administration of the therapeutic agents in animal models and healthy individuals. In general, the dose administered will vary between 10 μg-5 g/kg and more preferably between 100 μg-1 g/kg of bodyweight per day.

The therapeutic agent may be administered in combination with factor VIII (or a substitute of factor VIII). The dose of factor VIII administered together with the therapeutic agent may vary between 0.1 and 2000 Units per kg and more preferably between 1 and 200 Units per kg of body weight per day.

The words "substantially isolated form" as used herein are intended to refer to a form of the material which is different from any naturally occurring form of said material, i.e. different from the material in its natural environment. In particular, the words are intended to define relative freedom or absence of substances that naturally accompany the material.

EXAMPLE 1: Characterization of Anti-factor VIII Antibodies in Patient's Plasma Anti-factor VIII antibodies present in the plasma of a patient with acquired haemophilia were characterized by immunoprecipitation and neutralization experiments. The construction of recombinant factor VIII fragments corresponding to the A2, A3-C1-C2 and C2-domain of factor VIII has been described perviously (Fijnvandraat et al. 1997. Blood 89: 4371-4377; Fijnvandraat et al. 1998. Blood 91: 2347-2352). These recombinant factor VIII fragments were metabolically labelled with [$^{35}$S]-methionine and subsequently used for the detection of anti-factor VIII antibodies by immunoprecipitation using methods that have been described previously (Fijnvandraat et al. 1998. Blood 91: 2347-2352). Reactivity with both metabolically labeled A2, A3-C1-C2 and C2 domain was observed (data not shown). This indicates that at least two classes of antibodies directed against factor VIII were present in the plasma of the patient. To determine the contribution of the different antibodies in the patient's plasma to the titre of the inhibitor as measured in the Bethesda assay we performed neutralization experiments. Increasing concentrations of recombinant factor VIII fragments were mixed with samples that contained factor VIII antibodies diluted until a final inhibitory capacity of 2 BU/ml. Addition of both recombinant factor VIII light chain (A3-C1-C2) and C2-domain resulted in a decrease in the inhibitory activity of 50 and 20%, respectively. Addition of the factor VIII heavy chain (domains A1-A2-B) resulted in 45% neutralization of the inhibitor in the plasma of the patient. Based on these data we conclude that inhibitory antibodies directed against the heavy chain contribute for 45% to the inhibitory capacity of the patient's anti-factor VIII antibodies whereas anti-A3-C1-C2 antibodies account for the other half of the inhibitory capacity. Our results provide evidence for the occurrence of at least three classes of inhibitory antibodies in the patient's plasma. Next, we determined the subclass of the anti-factor VIII antibodies using methods that have been outlined previously (Fijnvandraat et al. 1997. Blood 89: 4371-4377). The antibodies with A2-specificity consisted predominantly of subclass IgG4; in addition small amounts of subclass IgG2 were observed. The antibodies directed against the factor VIII light chain consisted exclusively of subclass IgG4. The methods outlined above provide a starting point for further characterization of human antibodies with specificity for factor VIII. Similar analyses can be performed on samples derived of other patients which are analyzed for the presence of factor VIII inhibitors.

EXAMPLE 2: Construction of an IgG4 Specific Library

Peripheral blood lymphocytes were isolated from a blood sample of a patient with acquired haemophilia. The titre of the inhibitor was 1250 BU/ml. RNA was isolated from the lymphocytes using RNAzol (WAK Chemie, Germany) according to the instructions of the manufacturer. RNA was transcribed into cDNA employing random hexamer primers (Gibco, Breda, The Netherlands). Since, most of the anti-factor VIII antibodies described in Example 1 were of subclass IgG4, DNA fragments corresponding to the heavy chain of immunoglobulins of subclass IgG4 were amplified using the following set of oligonucleotide primers:

```
                                        (SEQ. ID. NO:1)
conIgG1-4     5' CTTGTCCACCTTGGTGTTGCTGGG 3'
                                        (SEQ. ID. NO:2)
huIgG4        5' ACGTTGCAGGTGTAGGTCTTC 3'
                                        (SEQ. ID. NO:3)
huVH1aback    5' CAGGTGCAGCTGGTGCAGTCTGG 3'
                                        (SEQ. ID. NO:4)
huVH2aback    5' CAGGTCAACTTAAGGGAGTCTGG 3'
                                        (SEQ. ID. NO:5)
huVH3aback    5' GAGGTGCAGCTGGTGGAGTCTGG 3'
                                        (SEQ. ID. NO:6)
huVH4aback    5' GAGGTGCAGCTGTTGCAGTCGGG 3'
                                        (SEQ. ID. NO:7)
huVH5aback    5' GAGGTACAGCTGCAGCAGTCTGC 3'
                                        (SEQ. ID. NO:8)
huVH6aback    5' CAGGTACAGCTGCAGCAGTCAGG 3'
                                        (SEQ. ID. NO:9)
huJH1-2forSal 5' GAGTCAT TCTCGT
                 GTCGACACGGTGACCAGGGT-
                 GCC 3'
                                        (SEQ. ID. NO:10)
huJH3forSal   5' GAGTCATTCTCGT
                 GTCGACACGGTGACCATTGT-
                 CCC 3'
                                        (SEQ. ID. NO:11)
huJH4-5forSal 5' GAGTCATTCTCGT
                 GTCGACACGGTGACCAGGGT-
                 TCC 3'
                                        (SEQ. ID. NO:12)
huJH6forSal   5' GAGTCATTCTCGT
                 GTCGACACGGTGACCGTGGT-
                 CCC 3'
                                        (SEQ. ID. NO:13)
huVH1backNco  5' AATCCATGGCCCAGGTGCAGCTGGTGCA 3'
                                        (SEQ. ID. NO:14)
huVH2backNco  5' AATCCATGGCCCAGGTCAACTTAAGGGA 3'
                                        (SEQ. ID. NO:15)
huVH3backNco  5' AATCCATGGCCGAGGTGCAGCTGGTGGA 3'
                                        (SEQ. ID. NO:16)
huVH4backNco  5' AATCCATGGCCGAGGTGCAGCTGTTGCA 3'
                                        (SEQ. ID. NO:17)
huVH5backNco  5' AATCCATGGCCGAGGTACAGCTGCAGCA 3'
                                        (SEQ. ID. NO:18)
huVH6backNco  5' AATCCATGGCCCAGGTACAGCTGCAGCA 3'
```

Oligonucleotide primers huVHa(1-6)back and huJH(1-6) for Sal (SEQ. ID. NOS: 9-12) have been described previously (Marks et al. 1991. J. Mol. Biol. 222: 581-597). Oligonucleotide primers huVH(1-6)backNco (SEQ. ID. NOS: 13-18) have been adapted from oligonucleotide primers described in the same paper. The first series of amplification involved primers huVH(1-6)back in conjunction with primer conIgG1-4 (SEQ. ID. NO: 1). Six different DNA fragments of about 700 bp, each corresponding to an individual VH-gene family were obtained. The six different fragments were isolated and re-amplified with primers huVH(1-6)back and primer huIgG4 (SEQ. ID. NO: 2). Six products of approximately 660 bp were obtained. The 6 different 660 bp fragments which represented the IgG4 repertoire of the patient were re-amplified with primers huVH(1-6)backNco (SEQ. ID. NOS: 13-18) and huJH(1-6) forSal (SEQ. ID. NOS: 9-12) in order to prepare these fragments for cloning. The resulting 24 fragments were pooled according to VH-gene family and the six different fragments were digested with NcoI and SalI. The digested fragments were purified and dissolved in TE (10 mM Tris-HCl pH=8.0; 0.1 mM EDTA). The vector pHEN-1-VLrep has been described previously (Griffin, H. M. and Ouwehand, W. H. 1995. Blood 86, 4430-4436; Schier et al. 1996. J. Mol. Biol. 225: 28-43) and contains a light chain repertoire derived of two non-immunized donors. Insertion of a heavy chain repertoire in this vector has been shown to result in the production of antibody fragments that consist of the variable domains of both heavy and light chain. These antibody fragments have been termed single chain Fv (scFv) fragments (Hoogenboom, H. R. et al. 1991. Nucleic Acid Res. 19: 4133-4137). The vector pHEN-1-VLrep (kindly provided by Dr. W. H. Ouwehand, Department of Transfusion Medicine, University of Cambridge, UK) was digested with XhoI and NcoI and the six fragments corresponding to the IgG4-specific heavy chain repertoire of the patient with acquired haemophilia were inserted. The ligation mixtures were transformed to *E. coli* TG1 and a library of 1,500,000-2,500,000 independent clones was obtained. Colonies were scraped and resuspended in 2TY supplemented with 15% glycerol, 100 μg/ml ampicillin and 1% glucose. Similar to the methods outlined above libraries that represent the immunoglobulin repertoire of other patients may be assembled.

EXAMPLE 3: Selection of Factor VIII Specific Antibodies

Selection of clones that encoded antibody fragments (scFvs) with factor VIII specificity was performed as outlined below. Glycerol stocks were plated onto 2TY plates that contained ampicillin (100 μg/ml) and 1% glucose. Colonies were grown overnight and scraped the next day and dissolved in 2TY supplemented with 100 μg/ml ampicillin and 1% glucose. These cells were diluted in 2TY supplemented with ampicillin (100 μg/ml) and 1% glucose till a final optical density (OD) of 0.3 (measured at 600 nm). Cells were grown at 37° C. till an OD of 0.5. Subsequently, 1 ml of culture was diluted 10 times in 2TY with ampicillin (100 μg/ml) and 1% glucose. Next, 20 μl of helper phage was added (VCSM13; $1 \times 10^{11}$ pfu/ml) and the mixture was incubated for 45 minutes at 37° C. without shaking. Then, cells were incubated at 37° C. with shaking at 150 rpm for another 45 minutes. The cells were spun down at low speed and resuspended in 100 ml of 2TY supplemented with ampicillin (100 μg/ml), 0.1% glucose and 25 μg/ml kanamycin. The cells were incubated overnight at 30° C. The next day cells were spun down at 10000 rpm for 30 minutes. The supernatant was harvested and recombinant phage were allowed to precipitate for 2 hours at 4° C. after the addition of 1/5 volume of 20% PEG6000/2.5 M NaCl. The phages were spun down (30 minutes 10000 rpm) and resuspended in 5 ml of TBS (50 mM Tris-HCl pH 7.4, 150 mM NaCl). This preparation was spun down for 5 minutes at 14000 rpm and the supernatant was stored at 4° C.

Selection of factor VIII-binding phages was performed as outlined below. Microtiter wells were coated overnight at 4° C. with 5 μg/ml of the murine factor VIII light chain specific monoclonal antibody CLB-CAg 12 which was diluted in 50 mM NaHCO$_3$ (pH 9.5). The wells were blocked for 1 hour at 37° C. with TBS containing 3% HSA. Phage solution ($1 \times 10^{12}$ pfu/ml) was diluted 1 to 1 in TBS supplemented with 6% HSA and 1% Tween-20 and incubated for 2 hours at room temperature with microtiter wells that contained immobilized CLB-CAg 12. The phage solution was removed and transferred to a second microtiter well (also coated with CLB-CAg 12) which had been preincubated with 1 μg/ml of factor VIII light chain. Phages were incubated with factor VIII light chain for 2 hours at room temperature. Wells were washed 20 times with TBS/0.1% Tween-20 and 20 times with TBS and bound phage was eluted with 100 mM triethylamine (pH 12). Eluted phage (volume 1 ml) was neutralized by the addition of 500 μl of 1 M Tris-HCl pH 7.4 and subsequently added to 5 ml of *E. coli* TG1 (OD 600=0.5). Cells were incubated for ½ hour at 37° C. (no shaking) and 10 minutes at 37° C. (shaken at 200 rpm). Cells were collected by centrifugation for 10 minutes at 4000 rpm for 7 minutes. Subsequently, infected TG1 cells were plated on 2TY agar plates supplemented with ampicillin (100 μg/ml) and 1.0% glucose. Cells were grown overnight at 30° C. Cells were scraped in 2TY supplemented with ampicillin (100 μg/ml), 1% glucose and 15% glycerol. Ampoules were stored at −70° C.

Alternatively, factor VIII light chain (5 μg/ml in 50 mM NaHCO$_3$ (pH 9.6)) was immobilized on immunotubes (Nunc, Life Technologies, Breda, The Netherlands). First, 1 ml of phage solution diluted in TBS supplemented with 3% HSA was incubated for 2 hours at room temperature in non-coated Immunotubes. Subsequently, 1 ml of phage solution was removed and incubated for 2 hours at room temperature in immunotubes coated with factor VIII light chain. Immunotubes were washed 20 times with TBS/0.1% Tween-20 and 20 times with TBS. Bound phage was eluted with 100 mM triethylamine (pH 12) and processed as outlined above.

Figure 2:
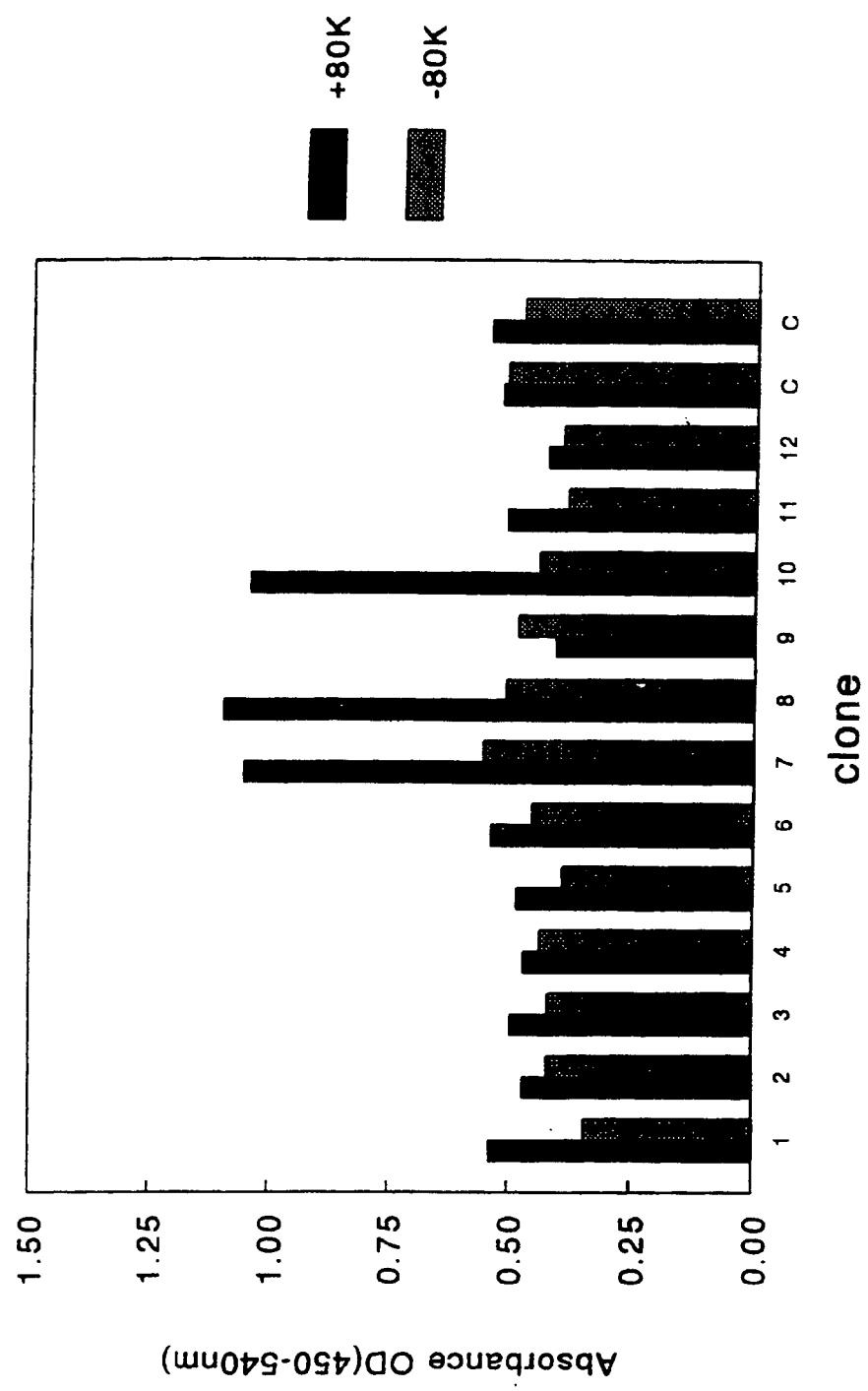
FIG. 2 shows the light chain specificity of 12 clones randomly chosen after the first round of panning of the IgG4-specific library described in Example 2. Clones 7, 8 and 10 express antibody fragments with factor VIII light chain specificity. The other clones do not specifically bind to the factor VIII light chain. Only background binding of the phage to the microtiter wells is observed (grey bars). Two clones (c) express antibody fragments that do not bind specifically to the factor VIII light chain.

The second round of panning was initiated by inoculating 50 μl of glycerol stock obtained after the first selection in 10 ml 2TY supplemented with ampicillin (100 μg/ml) and 1% glucose till a final OD600 of 0.3. Cells were grown till an OD600 of 0.5, diluted 1 to 10 in 2TY supplemented with ampicillin (100 μg/ml), kanamycin (25 μg/ml) and 1% glucose and subsequently infected with a 20 fold excess of VCSM13. Cells were grown overnight at 30° C. Supernatant containing the phage was harvested as described above and again screened for binding to immobilized factor VIII light chain. After found rounds of panning, 30 clones selected by ELISA and 30 clones that were obtained after panning with factor VIII light chain immobilized to immunotubes were grown and analyzed for binding to the factor VIII light chain. Colonies were picked and grown overnight in 2 ml 2TY supplemented with 100 μg/ml ampicillin and 1% glucose. The next day the cultures were diluted 200 times and grown till an OD600 of approximately 0.5. Cells were subsequently infected with VCSM13 for 45 minutes at 37° C. (no shaking) and 45 minutes at 37° C. (shaken at 200 rpm). Infected cultures were diluted 1 to 10 in 2TY supplemented with 100 μg/ml ampicillin, 0.1% glucose and 25 μg/ml kanamycin and cells were grown overnight at 30° C. Supernatant containing phage was collected after centrifugation and tested for binding to the factor VIII light chain as described below. The non-inhibiting murine monoclonal antibody CLB-CAg 12 directed against an epitope in the A3-C1 domain of factor VIII was immobilized on microtiter wells at a concentration of 5 μg/ml in 50 mM NaHCO$_3$ (pH 9.5). Wells were blocked for 1 hour in TBS supplemented with 3% HSA. Wells were incubated with factor VIII light chain at a concentration of 1 μg/ml in 50 mM Tris HCl (pH 7.4), 1 M NaCl, 2% HSA for 2 hours at 37° C. Fifty μl of phage solution and an equal volume of TBS supplemented with 1% Tween-20 and 6% HSA were added to wells containing factor VIII light chain. To monitor specific binding of the phages, wells that did not contain factor VIII light chain were incubated simultaneously with the same phage solution. Phage was incubated at room temperature for 2 hours and were shaken at regular intervals. Subsequently, wells were extensively washed 5 times with TBS supplemented with 0.1% Tween-20 and washed 5 times with TBS. The presence of bound phage was monitored by incubating with a peroxidase labelled polyclonal antibody directed against M13 (Pharmacia-LKB, Woerden, The Netherlands) in a dilution of 1 to 4000 in TBS supplemented with 1% HSA and 0.1% Tween-20. Plates were washed 5 times with TBS supplemented with 0.1% Tween-20 and 5 times with TBS. Binding of peroxidase-labelled anti-M13 antibody was quantified by incubation with 3-3'-5-5' tetramethylbenzidine (TMB). Substrate conversion was arrested by the addition of 100 µl of 2N $H_2SO_4$. Part of the results of this analysis are given in FIG. 1. An example of 12 clones that show specific binding to the factor VIII light chain is given. Clearly, phage encoded by clone 1 to 12 display binding to the factor VIII light chain (black bars). Some background binding is visible which is not dependent on the presence of the factor VIII light chain (grey bars). The bars labelled with c represent two clones that express antibody fragments that do not bind specifically to the factor VIII light chain. These clones have been derived from the initial library and have not been selected on the factor VIII light chain. To ensure that during subsequent rounds of panning an increase in the amount of factor VIII specific recombinant antibody fragments was obtained, we screened 12 clones obtained after the first round of panning for binding to the factor VIII light chain (FIG. 2). Only 3 out of 12 clones bind specifically to the factor VIII light chain. In 9 out of 12 clones binding of phage is not dependent on the presence of the factor VIII light chain. These results clearly indicate that during panning the amount of phages that express factor VIII-specific antibodies can be selectively enriched. In summary, we have outlined a specific protocol for the selection of factor VIII specific antibodies that correspond to the spectrum of anti-factor VIII antibodies present in the patient with acquired haemophilia. In the first two examples our analysis is limited to material derived of one single patient and only antibodies directed against the factor VIII light chain have been analyzed. Using the methods outlined in these two examples the repertoire of anti-factor VIII antibodies of other patients with an inhibitor can easily be obtained. Furthermore, anti-factor VIII antibodies directed against epitopes located outside the factor VIII light chain may be obtained by adapting the screening methods used in Example 1 and 2. Antibodies directed against the heavy chain can be selected by immobilizing factor VIII heavy chain employing monoclonal antibody CLB-CAg 9. In these two examples we have focused on the IgG4-repertoire of the patient. Similarly, other subclasses may be investigated using the appropriate primers. For example, subclass IgG1-4 can be detected by simply using primer conIgG1-4 (SEQ. ID. NO: 1) described in Example 1. Similarly, other primers specific for IgA, IgM, IgE and IgD may be utilized to assemble antibody-repertoires that include factor VIII-specific antibodies.

Figure 3:
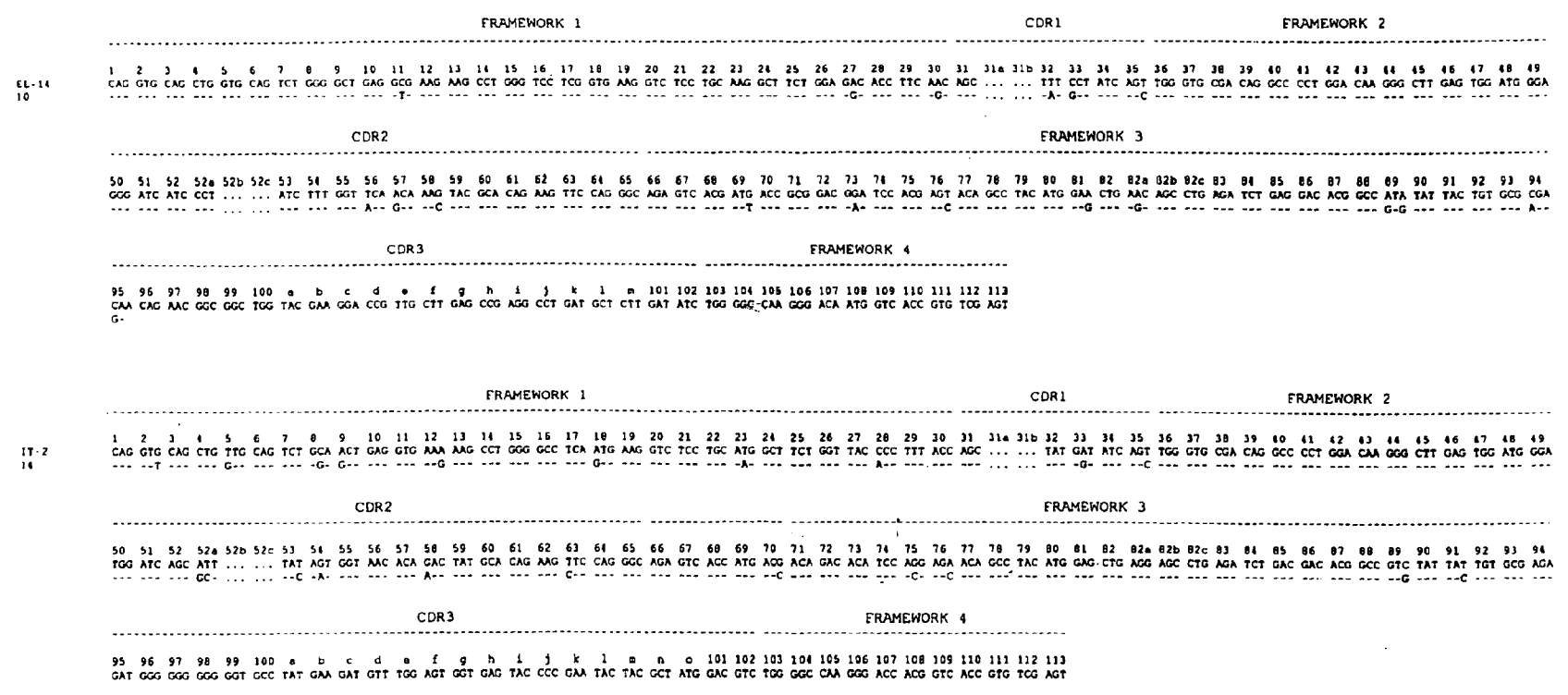

EXAMPLE 4: Sequence Characteristics of Recombinant Antibodies with Factor VIII Light Chain Specificity In the previous examples methods to obtain recombinant antibodies with factor VIII specificity has been outlined. To obtain information on the properties of these antibodies we selected 30 clones that have been selected by immobilized factor VIII in immunotubes. Also 30 clones which were selected employing factor VIII light chain with monoclonal antibody CLB-CAg 12 were analyzed. Clones were grown as descried in Example 2 and plasmid DNA was isolated. The nucleotide sequence of the variable part of the heavy chain (VH domain) of 55 clones was determined using fluorescently labelled M13 reverse primer on an ABI-Prism 377 DNA sequencer. The sequences obtained were aligned with heavy chain sequences in the database "V BASE" of the MRC Centre of Protein Engineering (Cambridge, UK). The 55 clones analyzed were encoded by two different VH-gene segments DP-10 (SEQ. ID. NO: 20) and DP-14 (SEQ. ID. NO: 22) (Cook and Tomlinson, Immunology Today 16: 237-242). The 41 clones that were encoded by the germline sequence DP14 (SEQ. ID. NO: 22) consisted of three groups of recombinant antibodies that differed mainly in the nucleotide sequences of the constant regions of the VH gene. Thirty-three clones which were represented by clone IT2, 5 clones were represented by EL25 and 3 clones were represented by clone EL5 (Table I). Two clones that were encoded by DP10 (SEQ. ID. NO: 20) (EL14) (SEQ. ID. NO: 19) and DP14 (SEQ. ID. NO: 22) (IT2) (SEQ. ID. NO: 21) were selected for further analysis. The nucleotide and primary amino acid sequence of these clones is listed in FIGS. 3 and 4. The characteristics of the two sequences are given in Table I. Part of clone EL14 is most likely derived of the D-segment D6-13 and J-segment JH-3b. Somatic hypermutation has occurred during the immune response as evidenced by the large number of nucleotide changes compared to the germline sequences of the VH segments. The variable heavy chain part of clone IT2 (SEQ ID. NO: 21) contains 20 nucleotide substitutions when compared to the germ line segment DP-14 (SEQ. ID. NO: 22). These 20 nucleotide substitutions result in a total of 13 amino acid changes (Table I). The variable heavy chain part of clone EL14 (SEQ. ID. NO: 19) contains 18 nucleotide substitutions when compared to the germ line segment DP-10 (SEQ. ID. NO: 20). These 18 nucleotide substitutions result in 12 amino acid changes (Table I). Clone IT2 has in part been derived from gene segments D3-3 and JH6b. Remarkably, a stretch of G-residues is observed between the germ line sequences DP14 (SEQ. ID. NO: 22) and D3-3 for clone IT2 that encodes for a flexable arm of glycine residues. Inspection of the amino acid sequence of clone EL14 (SEQ. ID. NO: 23) and IT2 (SEQ. ID. NO: 25) reveals several interesting features. Both CDR3 regions contain several glycine residues at their amino-terminal part which is in both cases followed by a tyrosine and a glutamic acid (GG-YE). Furthermore, a proline, alanine and an aspartic acid appear to be conserved in the carboxyl-terminal part of the CRD3 (P---A-D). A common motif can be derived from the amino acid sequences of the CDR3 regions of clone EL14 (SEQ. ID. NO: 23) and IT2 (SEQ. ID. NO: 25) which is given in FIG. 4B. These features may determine the specificity of these antibodies for the factor VIII light chain. In this example the nucleotide and primary amino acid sequence of two recombinant factor VIII antibodies has been disclosed. With methods similar to the ones described in this example recombinant antibodies that are directed against other regions on the factor VIII molecule may be analyzed. Common features of these antibodies can be identified as outlined in this example and therapeutic and diagnostic agents derived of these common features can be used for diagnosis and treatment of patients with factor VIII inhibitors.

EXAMPLE 5: Detection of Nucleotide Sequences of Factor VIII Specific Antibodies in Patient Samples The nucleotide and amino acid sequences outlines in the previous example can be used to specifically detect factor VIII antibodies with C2-specificity in heterogeneous mixtures of antibodies. This can be accomplished by developing reagents, for example, antibodies that specifically recognize the anti-factor VIII antibodies described in this invention. Detection of factor VIII-specific antibodies can also be performed by analysis of the presence of specific nucleotide sequences that encode factor VIII specific antibodies. Methods to obtain nucleotide sequences that encode factor VIII specific antibodies are disclosed in this invention. In this example the detection of nucleotide sequences encoding one of the factor VIII specific antibodies described in the previous example (EL14) (SEQ. ID. NO: 19) is disclosed. Lymphocytes of the patient with acquired haemophilia described in the first example were obtained. RNA was isolated and cDNA was prepared. Subsequently, DNA fragments were amplified with oligonucleotide primers huVH (1-6)aback (SEQ. ID NOS: 3-8) and conIgG1-4 (SEQ. ID. NO: 1) (see Example 2). The six different 700 bp fragments obtained were isolated and used for a second PCR with oligonucleotide primer huVH(1-6)aback (SEQ. ID. NOS: 3-8) and huIgG4 (SEQ. ID. NO: 2). This resulted in a fragment of 660 bp which was cloned into the vector pGEM-T (Promega, Madison, Wis., USA). The presence of nucleotide sequences that corresponded to that of clone EL14 (SEQ. ID. NO: 19) was addressed by nucleotide sequencing. One out of sixty clones analyzed did contain nucleotide sequences that were identical to that obtained for clone EL14 (SEQ. ID. NO: 19). This analysis shows that, using the nucleotide sequences disclosed in this invention as a starting point, it is possible to monitor the presence of factor VIII specific antibodies in patient samples. In this example oligonucleotide primers are used which have also been employed for the construction of the IgG4 specific library. Other combinations of oligonucleotide primers that are based on the nucleotide sequences of clone EL14 (SEQ. ID. NO: 19) and IT2 (SEQ. ID. NO: 21) may be designed which may include but are not limited to oligonucleotide primers that are based upon the CDR3 region of these antibodies. In this example detection of factor VIII specific antibodies is performed using analysis of nucleotide sequences. Alternatively, detection of factor VIII specific sequences may also be performed employing selective hybridization using probes that are based on the nucleotide sequence of the factor VIII specific antibodies disclosed in this invention. Other means of detection of specific nucleotide sequences that are known to an average expert in the art also fall within the scope of this invention. The methods disclosed in this invention allow for the isolation of factor VIII antibodies and determination of their nucleotide and amino acid sequence. In this example we have outlined described methods that detect factor VIII specific antibodies present in the repertoire of a patient with a factor VIII inhibitor. In examples 8 and 9 the nucleotide sequence of antibody fragments that bind to the A2- and A3-C1 domain of factor VIII is given. Methods similar to the ones described in this example can be used to detect nucleotide sequences that encode factor VIII inhibitors with A2-, A3-C1- or with a different epitope-specificity.

EXAMPLE 6: Properties of Factor VIII-specific Antibodies scFv-IT2 and scFv-EL14

Figure 5:
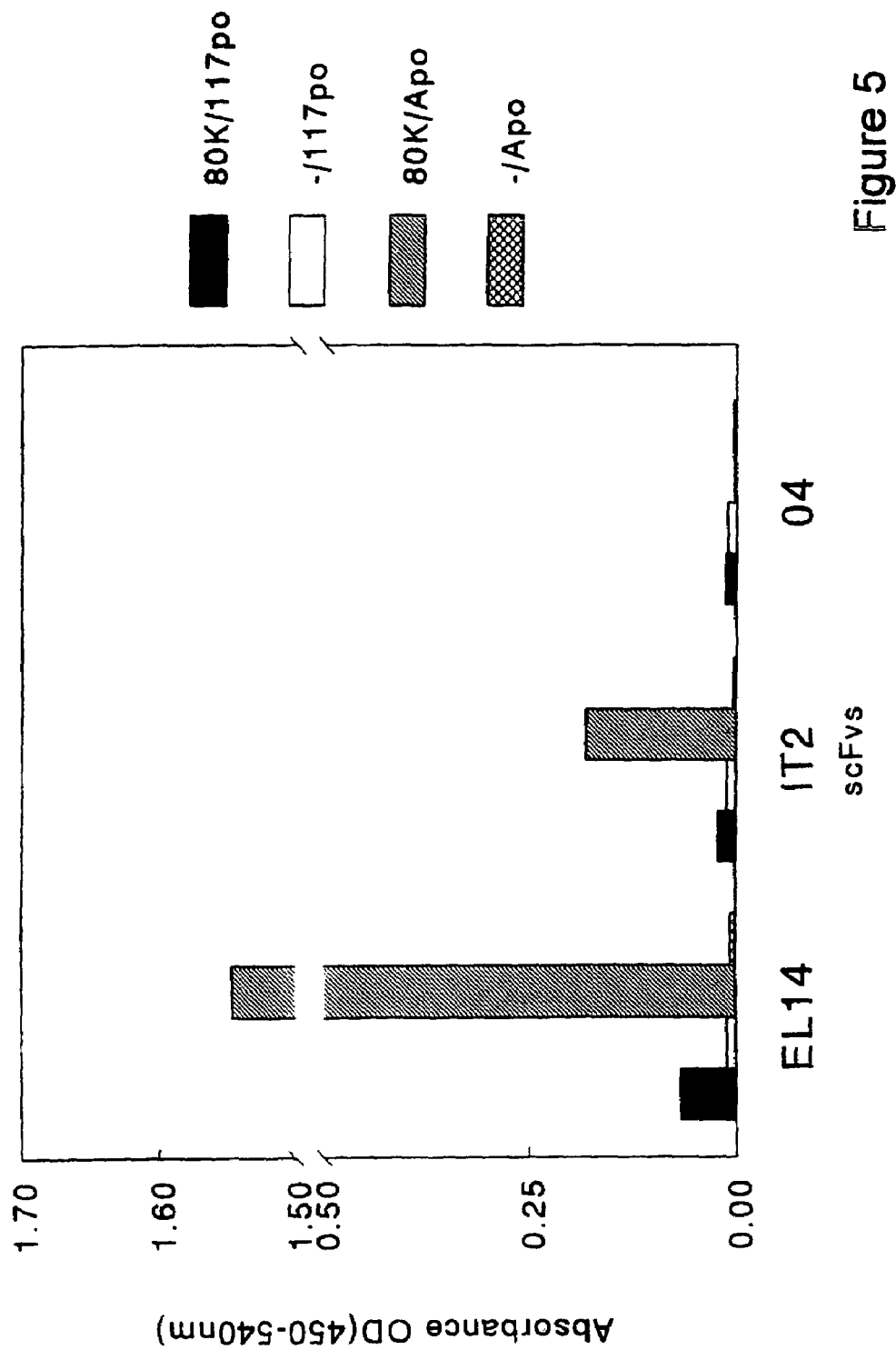
FIG. 5 shows the specificity of binding of scFv-EL14 and scFv-IT2 to the factor VIII light chain as assessed by the murine monoclonal antibodies CLB-CAg A and CLB-CAg 117. ScFv-EL14 binds specifically to the factor VIII light chain when peroxidase labelled CLB-CAg A (80K/Apo) is used as an indicator antibody (hatched bars). Also scFv-IT2 binds to the factor VIII light chain under these conditions (hatched bars). In contrast, when peroxidase labelled CLB-CAg 117 (80K/117po) is used as indicator antibody binding of scFv-EL14 and scFv-IT2 is strongly reduced (black bars). No binding is observed in the absence of factor VIII light chain (–/117po; –/Apo). Clone O4 does not bind to factor VIII under these experimental conditions. These experiments show that the epitope of scFv-EL14 and scFv-IT2 overlaps with that of CLB-CAg 117. On the y-axis the absorbance OD (450-540 nm) is given. On the x-axis scFv-EL14, scFv-IT2 and scFv-O4 are given.

The biochemical properties of the factor VIII specific antibodies IT2 and EL14 were characterized as follows. First, the plasmids pHEN-1-VL-EL14 and pHEN-1-VL-IT2 were digested with NcoI and NotI and the recombinant antibody fragments were isolated and cloned into the vector pUC119-sfi/Not-His6 (kindly provided by Dr. W. H. Ouwehand, University of Cambridge, Division of Transfusion Medicine, Cambridge UK). Positive clones were identified and grown till OD600 of 0.8-1.0 in 2TY medium supplemented with 1% glucose and 100 µg/ml ampicillin. Subsequently, Isopropyl-β-D-thiogalactopyranoside (IPTG) till a final concentration of 1 mM was added and cells were grown for 3 hours at 30° C. Cells were harvested by centrifugation for 15 minutes at 4000 g at 4° C. The pellet was dissolved in 10 ml of 30 mM Tris-HCl (pH 8.0), 1 mM EDTA and 20% sucrose in order to release the content of the periplasma. The mixture was incubated at 4° C. for 20 minutes and subsequently cells were collected by centrifugation (15 min 10800 g at 4° C.). The supernatant which consists primarily of proteins present in periplasma was collected. The pellet was resuspended in 10 ml 5 mM $MgSO_4$ and incubated for 20 minutes at 4° C. Residual cell debris was collected by centrifugation for 15 minutes at 10800 G. The supernatant (designated osmotic shock fraction) was collected and added to the fraction containing periplasma-derived proteins. The pooled fractions were centrifuged for 20 minutes at 30000 g at 4° C. and the supernatant was collected. The supernatant was filtered over a 0.22 µm filter. A mixture of protease inhibitors was added (Complete™ Mini, Boehringer Mannheim, Germany) and the pooled fractions were dialysed overnight against a buffer containing 50 mM NaPi (pH 7.4), 20 mM imidazole and 500 mM NaCl. ScFv's were purified by nickel affinity resin Ni-NTA (QIAGEN, Germany) as follows: 1 ml of Ni-NTA matrix was equilibrated with 50 mM NaPi (pH 7.4), 250 mM imidazole, 500 mM NaCl and subsequently with 50 mM NaPi (pH 7.4), 20 mM imidazole, 500 mM NaCl. Dialysed supernatant containing factor VIII specific scFv's were then batch-wise incubated with Ni-NTA matrix for 3 hours at 4° C. The Ni-NTA was then transferred to a column and washed with 7 ml of 50 mM NaPi (pH 7.4), 20 mM imidazole, 500 mM NaCl and 7 ml of 50 mM NaPi (pH 7.4), 35 mM imidazole, 500 mM NaCl. ScFv's were eluted with 50 mM NaPi (pH 7.4), 250 mM imidazole, 500 mM NaCl and stored at 4° C. The purity of the different scFv preparations was addressed by SDS-PAGE followed by staining with Coomassie Brilliant Blue. All purified ScFv's appeared for at least 90% homogenous and migrated with an apparent molecular weight of 30 kDa. In the preparations obtained a small amount of a protein with a lower molecular weight was observed. The identity of this band was investigated by immunoblotting with monoclonal antibody 9E10. The epitope of this antibody is present at the carboxyl-terminus of the scFV's. Both the protein migrating at a molecular weight of 30 kDa and 15 kDa reacted with monoclonal antibody 9E10 on Western blot. This indicates that the 15 kDa fragment most likely corresponds to the light chain of the scFv's. Purified scFv's corresponding to clone IT2 and EL14 were purified as outline above. A scFv derived of clone O4, a clone present in the patient library that did not bind to the factor VIII light chain was included as a negative control. The binding of scFv-IT2 and scFv-EL14 to the factor VIII light chain was addressed employing the following ELISA. Monoclonal antibody 9E10 (5 µg/ml) dissolved in 50 mM $NaHCO_3$ pH 9.5 was immobilized on microtiter wells overnight at 4° C. Subsequently, purified scFv's diluted in 50 mM Tris-HCl (pH 7.4), 150 mM NaCl, 1% HSA and 0.2% Tween-20 were added and incubated for 2 hours at room temperature. The microtiter plates were washed 5 times with TBS, 0.1% Tween-20. Next, purified factor VIII light chain was added (5 µg/ml) together with peroxidase labelled monoclonal antibody CLB-CAg A (0.5 µg/ml). The mixture (diluted in TBS, 0.1% Tween-20) was incubated for 2 hours at room temperature. The microtiter wells were washed 5 times with Tris-buffered saline (TBS) supplemented with 0.1% Tween-20 and 5 times with TBS. The amount of bound peroxidase labelled monoclonal antibody CLB-CAg A was quantified by the substrate TMB. The results of this analysis are given in FIG. 5. Both scFv-EL14 and scFv-IT2 react with specifically with the factor VIII light chain while scFv-04 did not react with the factor VIII light chain. Next, we used the factor VIII inhibitory murine monoclonal antibody CLB-CAg 117 for the detection of bound factor VIII light chain. The ELISA was performed as outlined above. Instead of peroxidase labelled CLB-CAg A we used peroxidase labelled CLB-CAg 117 for the detection of immobilized factor VIII light chain. We did not observe binding of CLB-CAg 117 when factor VIII light chain is immobilized by scFv-EL14 and scFv-IT2 (FIG. 5). These results show that the epitope of scFv-EL14 and scFv-IT2 overlaps with that of CLB-CAg 117. Previously, we have shown that the inhibitory antibody CLB-CAg 117 is directed against the C2-domain of factor VIII (Fijnvandraat et al. 1998. Blood 91: 2347-2352). Apparently, both scFv's bind to an epitope in the C2-domain of factor VIII which overlaps with that of the inhibitory murine monoclonal antibody CLB-CAg 117.

Figure 6:
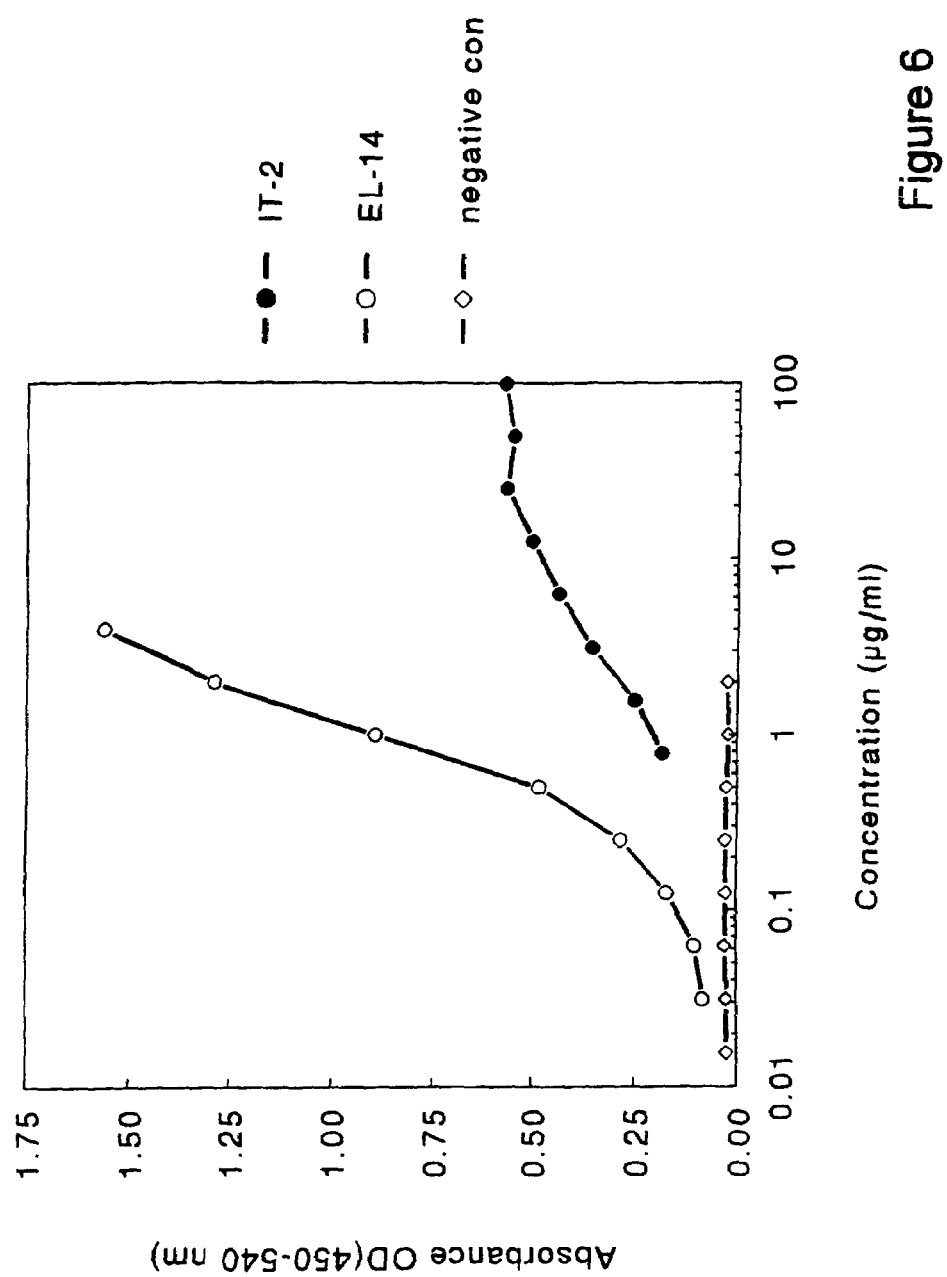
FIG. 6 shows the binding of different dilutions of purified scFv-EL14 (open circles), scFv-IT2 (closed circles) and scFv-O4 (negative control). On the x-axis the different concentrations of protein tested are indicated (μg/ml), on the y-axis the absorbance OD(450-540 nm) is given. Clone scFv-O4 does not bind to the factor VIII light chain at the protein concentration tested in this experiment. Both scFv-IT2 and scFv-EL14 bind to the factor VIII light chain. ScFv-EL14 binds with a higher affinity to the factor VIII light chain when compared scFv-IT2.

Next, different dilutions of scFv-EL14 and scFv-IT2 were tested for binding to immobilized factor VIII light chain as outlined above using CLB-CAg A as the detecting antibody (FIG. 6). From this analysis it appeared that scFv-EL14 binds with a higher affinity to the factor VIII light chain than scFv-IT2. These results were complemented by immuno-precipitation experiments for scFv-EL14. Immunoprecipitation experiments employing a metabolically labelled fragment corresponding to the C2-domain was performed essentially as described previously (Fijnvandraat et al. 1998. Blood 91: 2347-2352). Monoclonal antibody 9E10 was covalently linked to CNBr-activated Sepharose 4B and this matrix was used to bind scFv-EL14. Specific binding of scFv-EL14 to metabolically labelled C2-domain was detected and this confirms the C2-specificity of this recombinant antibody fragment. In this example methods have been disclosed to characterize recombinant antibodies with specificity for the C2-domain. In examples 8 and 9, we describe the nucleotide and amino acid sequence of recombinant antibody fragments that bind specifically to the A2 (SEQ. ID NOS: 49 and 51-55) and A3-C1 (SEQ. ID. NOS: 34, 36 and 39-48) domain of factor VIII. The methods described in this example can easily be adapted by an average expert skilled in the art, which will allow for characterization of recombinant antibodies directed against the A2 (SEQ. ID. NOS: 49 and 51-55), A3-C1 (SEQ. ID. NOS: 34, 36 and 39-48) or another epitope on factor VIII.

EXAMPLE 7: Factor VIII Specific Recombinant Antibody Fragments scFv-IT2 and scFv-EL14 Neutralize the Activity of Factor VIII Inhibitors In the previous example, we have shown the scFv-EL14 and scFv-IT2 bind to the factor VIII light chain and compete for binding with the murine inhibitory monoclonal antibody CLB-CAg 117. These observations suggest that the epitope of both scFv-EL14 and scFv-IT2 overlaps with that of CLB-CAg 117. It is expected that similar to CLB-CAg 117, scFv-EL14 and scFv-IT2 inhibit the biological activity of factor VIII. Increasing amounts of purified scFv's were tested for inhibition in the Bethesda assay. Surprisingly, addition of up to 170 µg/ml scFv did not result in factor VIII inhibition as measured in the Bethesda assay. In contrast, CLB-CAg 117 readily inhibited factor VIII when measured in the same assay. Apparently, binding of scFv-EL14 and scFv-IT2 to factor VIII does not interfere with the biological activity of factor VIII. This finding prompted us to investigate the capacity of both scFv-EL14 and scFv-IT2 to overcome inhibition by CLB-CAg 117. Monoclonal antibody CLB-CAg 117 was diluted till a final inhibitory activity of 2 BU/ml. This value corresponds with a residual factor VIII activity of 25% in the Bethesda assay. Subsequently, increasing concentrations of scFv-EL14 and scFv-IT2 were added. Surprisingly, both scFv-EL14 and scFv-IT2 could overcome the factor VIII inhibitory activity of CLB-CAg 117 (FIG. 7). ScFv-14 (panel A) proved to be more efficient than scFv-IT2 (panel B) in neutralizing the inhibitory activity of CLB-CAg 117. Both scFv-EL14 and scFv-IT2 were unable to neutralize the inhibitory activity of monoclonal antibody CLB-CAg A, directed against amino acid residues $Glu^{1811}$-$Lys^{1818}$ on the factor VIII light chain (Lenting et al. 1996. J. Biol. Chem. 271: 1935-1940). These results for the first time show that antibody fragments with factor VIII specificity can be used to interfere with the activity of factor VIII inhibitors. Administration of these antibody fragments will be beneficial for the treatment of patients with inhibitory antibodies directed against factor VIII. In this example the biological activity of antibody fragments with C2-specificity is disclosed. In examples 8 and 9, the nucleotide and amino acid sequence of recombinant antibody fragments that bind to the A2 (SEQ. ID. NOS: 49 and 51-55) and A3-C1 (SEQ. ID. NOS: 34, 36 and 39-48) domain of factor VIII is disclosed. The methods disclosed in this and the previous example can easily be adapted by an average expert skilled in the art to establish the capacity of recombinant antibody fragments directed against the A2 or A3-C1 domain to neutralize factor VIII inhibitors. Similar to outlined in this example recombinant antibody fragments that bind to other regions can be evaluated for their neutralizing capacity of factor VIII inhibitors. Similarly to what has been described in this example for scFv-EL14 and scFv-IT2, antibody fragments binding to A2, A3-C1 and other domains on factor VIII can be used for treatment of patients with factor VIII inhibitors.

EXAMPLE 8: Isolation and Characteristics of Anti-factor VIII Antibodies that Specifically Bind to the A3-C1 Domain of Factor VIII Previous studies have indicated that plasma of a substantial number of inhibitor patients contains anti-factor VIII antibodies that bind specifically to the A3-C1 domains of factor VIII (Fijnvandraat et al. 1998. Blood 91: 2347-2352: Zhong et al. 1998. Blood 92: 136-142). Here, we have employed phage display technology to isolate anti-factor VIII antibodies from the total immunoglobulin repertoire of a haemophilia A patient with an inhibitor. Previously, we have shown that in plasma of this patient anti-factor VIII antibodies directed against the factor VIII light chain are present. The majority of the anti-factor VIII antibodies in this patient is directed against the A3-C1 domain whereas a small portion of anti-factor VIII antibodies reacts with the C2-domain (Fijnvandraat et al. 1998. Blood 91: 2347-2352). The majority of anti-factor VIII antibodies were of subclass IgG4. An IgG4-specific library was constructed using peripheral blood lymphocytes of the patient as starting material. A library consisting of $1.9 \times 10^6$ independent clones was obtained using the methods outlined in Example 2. Selection of recombinant phage that bind specifically to factor VIII was performed essentially as outlined in Example 3.

Microtiter wells were coated overnight at 4° C. with 5 µg/ml of the murine factor VIII light chain specific monoclonal antibody CLB-CAg 117 which was diluted in 50 mM NaHCO$_3$ (pH 9.5). Monoclonal antibody CLB-CAg 117 is directed against the C2-domain of factor VIII. The use of CLB-CAg 117 in the selection-protocol may result in elimination of recombinant phages that express immunoglobulin fragments directed against the C2-domain of factor VIII. Recombinant phages expressing the IgG4 specific immunoglobulin repertoire were prepared as described in Example 3. Recombinant phages were initially incubated on microtiter wells that contained immobilized CLB-CAg 117 for 2 hours in TBS supplemented with 3% HSA and 0.5% Tween-20. The phage solution was removed and transferred to a second microtiter well (also coated with CLB-CAg 117) which had been preincubated with 1 µg/ml of factor VIII light chain. Phages were allowed to bind to the immobilized factor VIII light chain for 2 hours at room temperature. Wells were washed extensively as described in Example 3 and bound phage were eluted with 100 mM triethylamine (pH 12). The eluted phage were neutralized by the addition of 1 M Tris-HCl pH 7.4 and the resulting solution was used to infect *E. coli* TG1 cells as described in Example 3.

Alternatively, purified factor VIII (5 µg/ml in 50 mM NaHCO$_3$ (pH 9.6)) was immobilized on immunotubes (Nunc, Life Technologies, Breda, The Netherlands). Recombinant phages diluted in TBS supplemented with 3% HSA were first incubated for 2 hours at room temperature in non-coated immunotubes. Subsequently, 1 ml of phage solution was removed and incubated for 2 hours at room temperature in Immunotubes coated with factor VIII. Following extensive washing (20 times with TBS/0.1% Tween-20 and 20 times with TBS) bound phage were eluted with 100 mM triethylamine (pH 12) and processed as outlined above.

Figure 8:
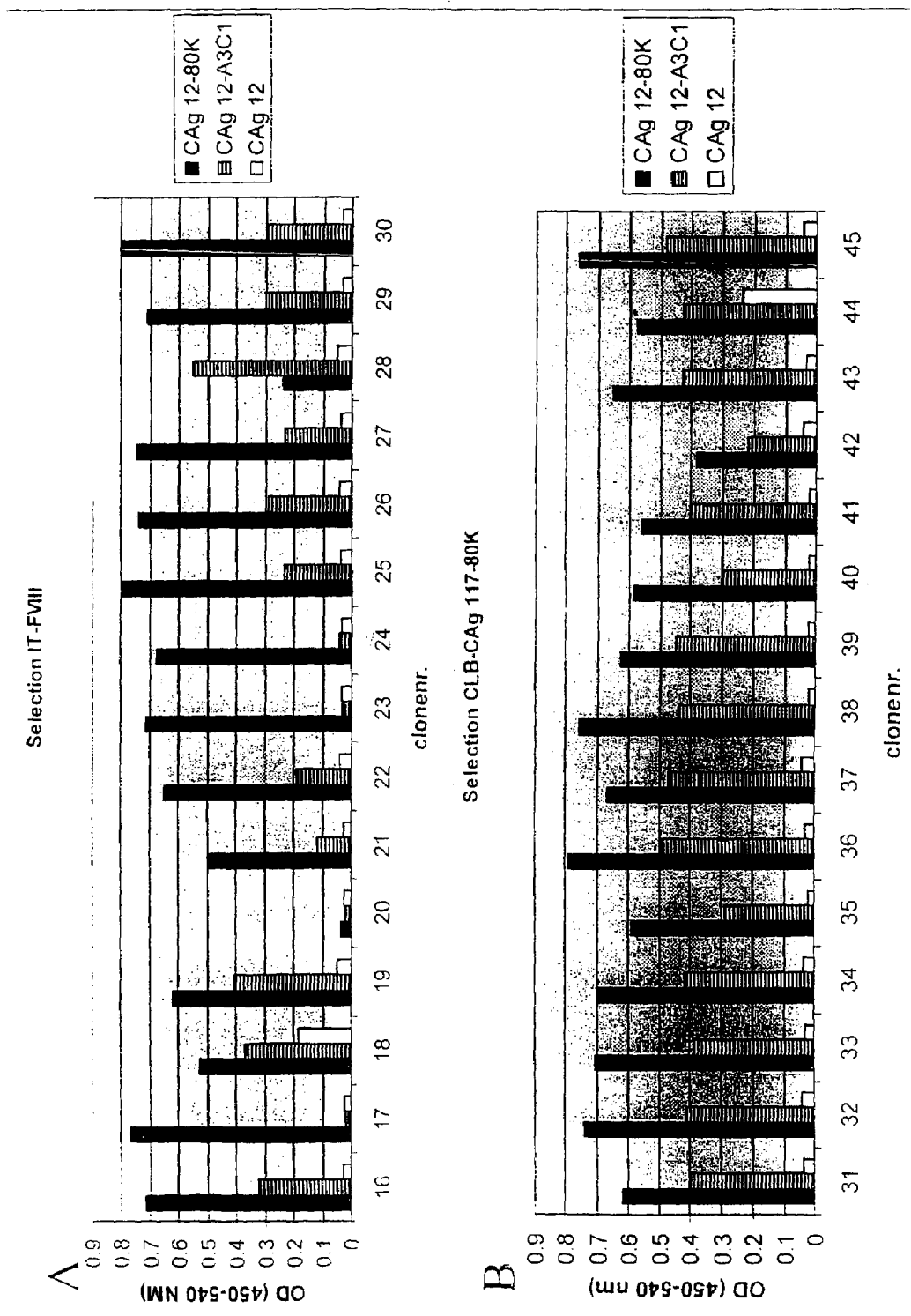
FIG. 8A shows the epitope specificity of 15 clones obtained after four rounds of panning of the IgG4-specific library described in example 8. Panning was performed using factor VIII immoblized on immunotubes. Phage expressing recombinant antibodies were incubated on microtiter wells which contained factor VIII light chain (black bars) or A3-C1-domain (hatched bars). To correct for background binding, phage were also incubated on microtiter wells that did not contain factor VIII light chain or A3-C1 domain (white bars). On the y-axis the OD (450-540 nm) is depicted.
FIG. 8B shows the epitope specificity of 15 clones obtained after four rounds of panning the IgG4 specific library described in example 8. Panning was performed using factor VIII light chain that had been immoblized in microtiter wells employing CLB-CAg 117. Phage expressing recombinant antibodies were incubated on microtiter wells which contained factor VIII light chain (black bars) or A3-C1-domain (hatched bars). To correct for background binding, phage were also incubated on microtiter wells that did not contain factor VIII light chain or A3-C1 domain (white bars). On the y-axis the OD (450-540 nm) is depicted.

The second, third and fourth round of panning were performed using the selection protocol described above. After the fourth round of panning 15 individual clones were picked and recombinant phage were tested for binding to the factor VIII light chain and the A3-C1 domain. Factor VIII light chain was purified as described previously. A construct expressing recombinant A3-C1 domain was prepared essentially as described previously (Sawamoto et al. 1998. Thrombosis and Haemostasis vol. 78, 62-68) and expressed in CHO-cells. The non-inhibitory murine monoclonal antibody CLB-CAg 12 directed against an epitope in the A3-C1 domain of factor VIII was immobilized on microtiter wells at a concentration of 5 µg/ml in 50 mM NaHCO$_3$ (pH 9.5). Wells were blocked for 1 hour in TBS supplemented with 3% HSA. Subsequently, wells were incubated with factor VIII light chain (1 µg/ml) or recombinant A3-C1 domain (0.06 nM) in 50 mM Tris HCl (pH 7.4), 1 M NaCl, 2% HSA for 2 hours at 37° C. Fifty µl of phage solution and an equal volume of TBS supplemented with 1% Tween-20 and 6% HSA were added to wells containing immobilized factor VIII light chain or A3-C1 domain. To monitor specific binding of the phage, wells that did not contain factor VIII light chain or recombinant A3-C1 domain were incubated with simultaneously with the phage solution. Phage were incubated at room temperature for 2 hours and were shaken at regular intervals. Wells were washed extensively with TBS supplemented with 0.1% Tween-20. The presence of bound phage was monitored as described in Example 3. The results of the analysis are depicted in FIG. 8. In panel A, 15 clones selected in immunotubes that contain factor VIII are depicted. Of the 15 clones analyzed, 1 clone (clone 20) did not react with factor VIII light chain and recombinant A3-C1 domain suggesting that this clone does not encode an antibody fragment with specificity for the A3-C1 domain of factor VIII. Three clones (clone 17, 23 and 24) do react with the factor VIII light chain but fail to react with recombinant A3-C1 domain. Apparently, the epitope of these recombinant antibody fragments is localized in the C2-domain of factor VIII. The remaining 11 clones react both with the factor VIII light chain and the recombinant A3-C1 domain. In panel B, 15 clones selected in microtiter wells that contain CLB-CAg 117 and factor VIII light chain are depicted. Clones 31-45 all interact with the factor VIII light chain (black bars) and recombinant A3-C1 domain (hatched bars). This analysis shows that phage derived of clone 31-45 encode antibody fragments that bind specifically to the A3-C1 domain of factor VIII.

These results show that the protocol outlined above is suitable for the selection of recombinant antibody fragments that bind specifically to the A3-C1 domain of factor VIII. Using the methods disclosed in this example, it is feasible to isolate recombinant phage encoding antibody fragments specific for the A3-C1 domain from other patients with factor VIII inhibitors.

The nucleotide sequence of the variable heavy chain fragments of 26 clones that reacted specifically with recombinant A3-C1 domain was determined essentially as described in Example 4. The sequences obtained were aligned with heavy chain sequences in the database "V BASE" of the MRC Centre of Protein Engineering (Cambridge, UK). The 26 clones analyzed were encoded by four different VH-gene segments DP15 (SEQ. ID. NO: 31), DP31 (SEQ. ID. NO: 33) and DP49 (SEQ. ID. NO: 35) and DP77 (SEQ. ID. NO: 37). The amino acid sequence of the variable heavy chain fragments of clones B38 (SEQ. ID. NO: 32), B18 (SEQ. ID. NO: 34), B35 (SEQ. ID. NO: 36) and B04 (SEQ. ID. NO: 38) is listed in FIG. 9A. The nucleotide sequence of these four clones is presented in FIGS. 9B-E (SEQ. ID. NOS: 39, 42, 44 and 46).

EXAMPLE 9: Isolation and Characteristics of Anti-factor VIII Antibodies that Bind to the A2-domain of Factor VIII An immunodominant region which constitutes a binding site for factor VIII inhibitors has been localized to the A2-domain of factor VIII (Healey et al. 1995, J. Biol. Chem. 270: 14505-14509). We characterized the anti-factor VIII antibodies in plasma of a patient with mild haemophilia A and an inhibitor, essentially as outlined in example 1. Recombinant factor VIII fragments corresponding to the A2, A3-C1-C2 and C2-domain of factor VIII were metabolically labelled with [$^{35}$S]-methionine and used for the detection of anti-factor VIII antibodies in the patient's plasma. Reactivity with metabolically labelled A2-domain and A3-C1-C2 domain was observed whereas only weak reactivity with metabolically labelled C2-domain was observed (data not shown). To determine the inhibitory capacity of both the anti-A2 and anti-A3-C1-C2 antibodies we performed neutralization experiments. The factor VIII inhibitor was diluted until a final value of 2 BU/ml and subsequently increasing amounts of recombinant A2 or A3-C1-C2 were added. Addition of recombinant A2-domain resulted in almost complete neutralization of the factor VIII inhibitors present in patient's plasma. Addition of recombinant A3-C1-C2 only neutralized the factor VIII inhibitor to a limited extent (<10%). These results show that the majority of factor VIII inhibitors are directed towards the A2-domain of factor VIII. We assessed the subclass of the anti-factor VIII antibodies by enzyme linked sorbent assay. Both anti-A2 and anti-A3-C1-C2 antibodies consisted predominantly of subclass IgG4.

Peripheral blood lymphocytes of the patient were used to construct an IgG4-specific library as outlined in example 2. A library consisting of $1.9 \times 10^6$ clones was obtained. Recombinant phage expressing the IgG4-specific immunoglobulin repertoire of the patient were prepared as described in Example 3. Selection of phages binding to the A2-domain of factor VIII was performed by one of the following methods:

1. Purified factor VIII heavy chain (10 µg/ml) was immobilized on immunotubes (Nunc, Life Technologies, Breda, The Netherlands) in 50 mM NaHCO$_3$ (pH 9.5). Recombinant phages diluted in TBS supplemented with 3% HSA were first incubated for 2 hours at room temperature in non-coated immunotubes. Non-bound phage were transferred to an immunotube coated with factor VIII. Following extensive washing (20 times with TBS/0.1% Tween-20 and 20 times with TBS) bound phage was eluted with 100 mM triethylamine (pH 12). Eluted phage was neutralized by the addition of 1 M Tris-HCl pH 7.4 and used to infect *E. coli* TG1 cells as described in Example 3.

2. Alternatively, the murine monoclonal antibody CLB-CAg 9, directed against amino acid sequence 713-740 in the A2-domain of factor VIII was immobilized on microtiter wells at a concentration of 5 µg/ml in 50 mM NaHCO$_3$ (pH 9.6). Purified factor VIII heavy chain (1 µg/ml) was then added and allowed to bind to CLB-CAg 9. Recombinant phage diluted in TBS 3% HSA and 0.5% Tween 20 were first incubated in microtiter wells containing only immobilized CLB-CAg 9. After 2 hours non-bound phage were transferred to a microtiter well which contained immobilized factor VIII heavy chain. Phage were allowed to bind to the factor VIII heavy chain for 2 hours at room temperature. Wells were washed extensively (see above) and finally bound phage were eluted with 100 mM triethylamine (pH 12) and processed as outlined above.

Figure 10:
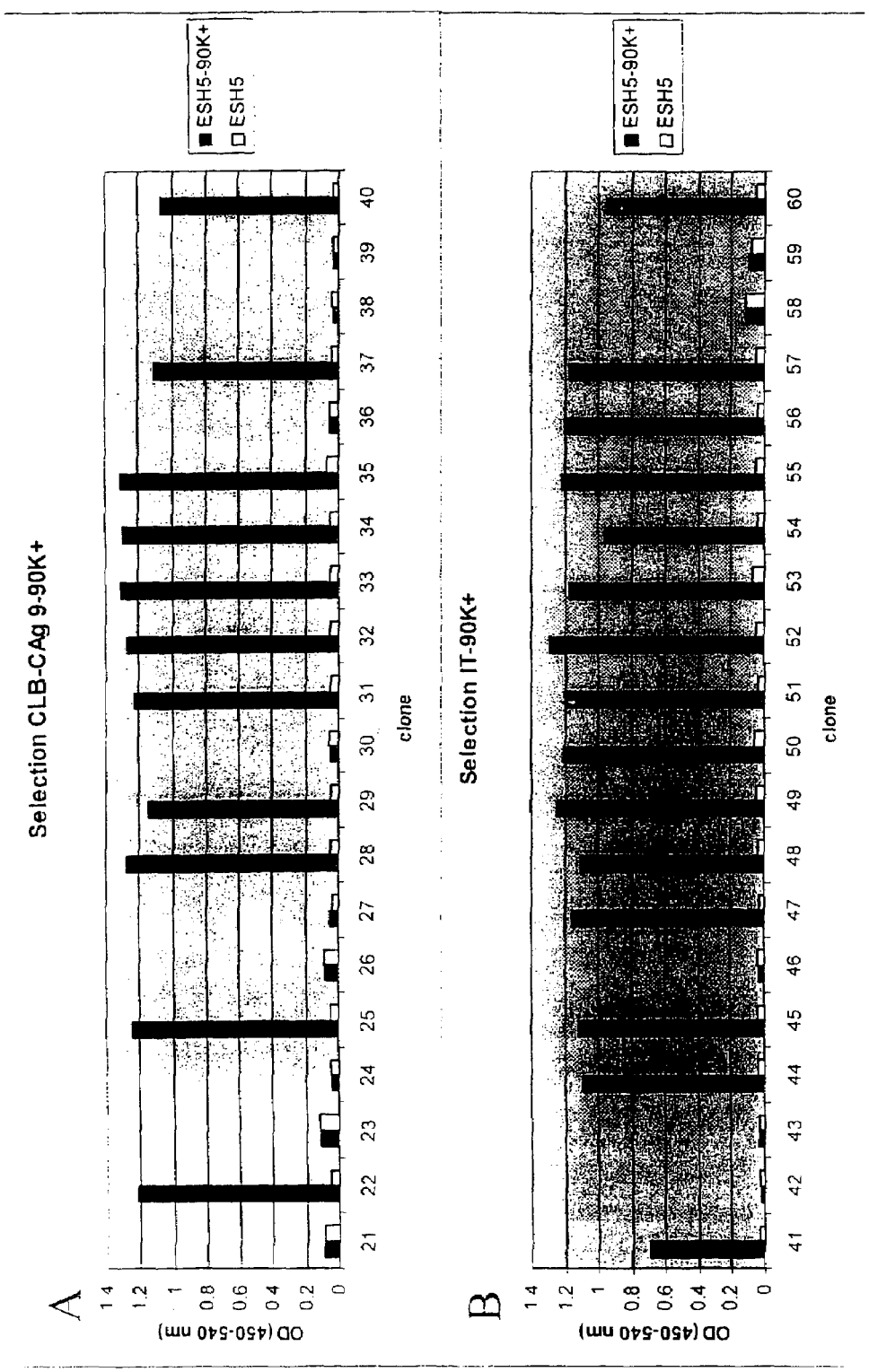
FIG. 10A shows the epitope specificity of 20 clones obtained after four rounds of panning of the IgG4-specific library described in Example 9. Panning was performed using factor VIII heavy chain (90K+) that had been immobilized in microtiter wells employing CLB-CAg 9. Phage expressing recombinant antibodies were incubated on microtiter wells which contained factor VIII heavy chain that was immobilized using the anti-heavy chain monoclonal antibody ESH5 (black bars). To correct for background binding, phage were also incubated on microtiter wells did not contain factor VIII heavy chain (white bars). On the y-axis the OD (450-540 nm) is depicted.
FIG. 10B shows the epitope specificity of 20 clones obtained after four rounds of panning of the IgG4-specific library described in Example 9. Panning was performed using factor VIII heavy chain (90K+) that had been immobilized in immunotubes. Phage expressing recombinant antibodies were incubated on microtiter wells which contained factor VIII heavy chain that was immobilized using the anti-heavy chain monoclonal antibody ESH5 (black bars). To correct for background binding, phage were also incubated on microtiter wells that did not contain factor VIII heavy chain (white bars). On the y-axis the OD (450-540 nm) is depicted.

After four rounds of selection individual clones were picked and binding of recombinant phage to factor VIII heavy chain was evaluated by an enzyme linked immuno sorbent assay. Monoclonal antibody ESH5 (American Diagnostica, Greenwich, Conn., USA) was immobilized onto microtiter wells at a concentration of 5 µg/ml in 50 mM NaHCO$_3$ (pH 9.6). Purified factor VIII heavy chain (1 µg/ml) was added and incubated for 2 hours at 37° C. Subsequently, recombinant phage, diluted 1 to 1 in 50 mM Tris-HCl pH 7.4, 1 M NaCl and 2% HSA, was added and incubated for 2 hours at room temperature. The amount of recombinant phage bound was determined was determined as described in Example 3. The results of the analysis is given in FIG. 10. Twenty clones which were selected in microtiter wells in which factor VIII heavy chain was immobilized by CLB-CAg 9 were analyzed. Eleven out of 20 clones bound specifically to the heavy chain of factor VIII (FIG. 10A). Clones that were selected by immobilized factor VIII heavy chain in immunotubes were also analyzed. Fifteen out of 20 clones bound specifically to the factor VIII heavy chain (FIG. 10B). These results show that the protocol outlined above permits the isolation of anti-factor VIII antibodies that are directed against the heavy chain (A1-A2) of factor VIII. Using the methods disclosed in this example it is feasible to isolate anti-factor VIII antibodies from the repertoire of additional patients with factor VIII inhibitors directed against the A2-domain.

The nucleotide sequence of the variable heavy chain fragments of 26 clones that reacted specifically with the factor VIII heavy chain were determined essentially as described in Example 4. The sequences obtained were aligned with heavy chain sequences in the database "V BASE" of the MRC Centre of Protein Engineering (Cambridge, UK). The 26 clones analyzed were encoded by two different VH-gene segments DP10 SEQ. ID. NO: 24) and DP47 (SEQ. ID. NO: 50) (FIG. 11A). The nucleotide sequence of the variable heavy chain of these clones is listed in FIG. 11B (SEQ. ID. NO: 52) and C (SEQ. ID. NO: 54).

EXAMPLE 10: Factor VIII Specific Recombinant Antibody Fragments can Neutralize the Activity of Factor VIII Inhibitors Present in Plasma of Patients with Haemophilia In example 7, we have shown that scFv-EL14 and scFv-IT2 neutralize the inhibitory activity of the murine monoclonal antibody CLB-CAg 117. We tested whether scFv-EL14 can also neutralize factor VIII inhibitors present in plasma of haemophilia A patients. First, we tested plasma of the patient with acquired haemophilia from whom the recombinant antibody fragments were derived. As described in example 1, recombinant C2-domain was capable of neutralizing 20% of the factor VIII inhibitor in patient's plasma (Table III). The effect of scFv-EL14 was evaluated in a similar set-up. Plasma was diluted till a final value of 2 BU/ml and increasing amounts of scFv-EL14 were added. ScFv-EL14 could neutralize about 20% of the total activity of factor VIII inhibitor in patient's plasma. These results suggest that scFv directed against the C2-domain prevent binding of factor VIII inhibitory antibodies that bind to the C2-domain of factor VIII.

Next, we tested two plasma samples derived of patients with congenital haemophilia A and factor VIII inhibitors. The relative contribution of the C2-domain to the total amount of factor VIII inhibitor for both samples ranged between 40% and 90%. Neutralization experiments indicate that addition of increasing concentrations of scFv-EL14 results in significant reduction of the levels of factor VIII inhibitor in plasma of these two patients with congenital haemophilia A. These results confirm that scFv-EL14 alleviates binding of human factor VIII inhibitors to the C2-domain. Our findings show that scFv-EL14 shields antigenic sites that are present in the C2-domain of factor VIII. This property of scFv-EL14 can be utilized to prevent binding of factor VIII inhibitors to the C2-domain of administered factor VIII in haemophilia A patients with an inhibitor. It has been firmly established that factor VIII inhibitors often recognize multiple epitopes that have been localized to the A2-, A3- and C2 domain of factor VIII. In this example the neutralizing activity of the C2-domain specific scFv-EL14 on the biological activity of factor VIII inhibitors is described.

In examples 8 and 9 we have disclosed methods to obtain recombinant antibodies that specifically react with the A3-C1 domain and heavy chain (A1-A2) of factor VIII. In this example, we have shown that recombinant antibodies directed against the C2-domain of factor VIII can shield antigenic sites on factor VIII. Similarly, anti-A3-C1 antibodies and anti-A2-antibodies described in examples 8 and 9 can be tested for their ability to compete with factor VIII inhibitors for binding to factor VIII. The anti-A3-C1 and anti-A1-A2 antibodies disclosed in this invention may also be used for treatment of patients with inhibitors, which react with the A3-C1 and/or the A1-A2-domain.

TABLE I

Nucleotide sequences of clones expressing recombinant antibodies with specificity for the factor VIII light chain. Based on the nucleotide sequence 55 of the 60 clones analyzed could be arranged as depicted below. In the first column clones with the same nucleotide sequence are arranged in four groups. The number of clones corresponding to this group is given in brackets. Clone EL5 (SEQ. ID. NO:27), EL25 (SEQ. ID. NO: 28) and IT2 (SEQ. ID. NO:25) are related as indicated in Figure 4B.
In the second column the heavy chain family to which these clones belong is depicted. All clones analyzed belong to the VH1-family. In the third column the germline segment is depicted. Clone EL5 (SEQ. ID. NO:27), E125 (SEQ. ID. NO:28) and IT2 (SEQ. ID. NOS:21, 25) belong to germline segment DP-14 (SEQ. ID. NOS:22, 26) while clone EL14 (SEQ. ID. NOS:19, 23) belongs to germline sequence DP-10 (SEQ. ID. NOS:20, 24).
In the fourth column the number of mutations in the different clones is depicted. The first number corresponds to the number of nucleotide mutations while the second one corresponds to the number of amino acid changes. The sequences were compared with the nucleotide and amino acid sequences of the germline segments indicated in the Table.

| Clone | VH family | Germline segment | Mutations |
|-------|-----------|------------------|-----------|
| EL5 (3) | VH1 | DP-14 | 20/12 |
| EL14 (14) | VH1 | DP-10 | 18/12 |
| EL25 (5) | VH1 | DP-14 | 19/11 |
| IT2 (33) | VH1 | DP-14 | 20/13 |

The invention claimed is:

1. An isolated antibody or fragment thereof capable of specific binding to factor VIII and comprising a heavy chain variable region of a human antibody with factor VIII specificity and a light chain variable region of a human antibody, wherein the heavy chain variable region comprises a sequence selected from the group consisting of SEQ. ID. NO: 23, SEQ. ID. NO: 25, SEQ. ID. NO: 32, SEQ. ID. NO: 34, SEQ. ID. NO: 36, SEQ. ID. NO: 38, SEQ. ID. NO: 49, and SEQ. ID. NO: 51.

2. The isolated antibody or fragment thereof of claim 1, which is capable of interfering with the activity of factor VIII inhibitors, and wherein the heavy chain variable region comprises a sequence selected from the group consisting of SEQ. ID. NO: 25 and SEQ. ID. NO: 23.

3. The isolated antibody or fragment thereof of claim 1, wherein the heavy chain variable region comprises a sequence selected from the group consisting of SEQ. ID. NO: 32, SEQ. ID. NO: 34, SEQ. ID. NO: 36, SEQ. ID. NO: 38, SEQ. ID. NO: 49 and SEQ. ID. NO: 51.

4. The isolated antibody or fragment thereof of claim 1, wherein said polypeptide is a single chain Fv fragment.

5. The isolated antibody or fragment thereof of claim 1, wherein said polypeptide is an antibody.

6. The isolated antibody of fragment thereof of claim 5, wherein said antibody is an IgG.

7. The isolated antibody or fragment thereof of claim 1, wherein said polypeptide specifically binds the heavy chain of factor VIII.

8. The isolated antibody or fragment thereof of claim 1, wherein said polypeptide specifically binds a domain of the heavy chain of factor VIII consisting of the A1 domain, the A2 domain and the B domain of factor VIII.

9. The isolated antibody or fragment thereof of claim 1, wherein said polypeptide specifically binds the light chain of factor VIII.

10. The isolated antibody or fragment thereof of claim 1, wherein said polypeptide specifically binds a region of the light chain of factor VIII consisting of the A3 domain, the C1 domain and the C2 domain of factor VIII.

11. A composition comprising the isolated antibody or fragment thereof according to claim 1 together with a pharmaceutically acceptable carrier.

12. A composition comprising the isolated antibody or fragment thereof according to claim 3 together with a pharmaceutically acceptable carrier.

13. A composition comprising the isolated antibody or fragment thereof according to claim 2 together with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 7,364,735 B1 | Page 1 of 1 |
| APPLICATION NO. | : 09/674752 | |
| DATED | : April 29, 2008 | |
| INVENTOR(S) | : Voorberg et al. | |

It is certified that error appears in the above-identified patent and that said Letters Patent is hereby corrected as shown below:

COVER PAGE ITEM [74]:

Now reads: "(74) *Attorney, Agent, or Firm* - Hoffman & Baron, LLP"

Should read: --*Attorney, Agent, or Firm* - Hoffmann & Baron, LLP--

IN THE SPECIFICATION:
Column 4, line 17:

Now reads: "with factor VIII specificity."

Should read: --with factor VIII specificity or an anti-idiotypic antibody directed against a human antibody with factor VIII specificity.

Column 4, line 38:

Now reads: "(black bars; '80K)"

Should read: --(black bars; +80K)--

Column 4, line 41:

Now reads: "(grey bars; +80K)"

Should read: --(grey bars; -80K)--

Signed and Sealed this

Sixteenth Day of September, 2008

JON W. DUDAS
*Director of the United States Patent and Trademark Office*